US010167494B2

(12) United States Patent
Walsh et al.

(10) Patent No.: US 10,167,494 B2
(45) Date of Patent: *Jan. 1, 2019

(54) METHOD FOR DETECTION, CHARACTERIZATION AND/OR IDENTIFICATION OF MICROORGANISMS IN A SEALED CONTAINER

(75) Inventors: John Walsh, Durham, NC (US); Jones M. Hyman, Wake Forest, NC (US); Thurman Thorpe, Durham, NC (US); Bradford Clay, Wildwood, MO (US)

(73) Assignee: bioMerieux, Inc., Durham, NC (US)

( * ) Notice: Subject to any disclaimer, the term of this patent is extended or adjusted under 35 U.S.C. 154(b) by 1408 days.

This patent is subject to a terminal disclaimer.

(21) Appl. No.: 12/589,968

(22) Filed: Oct. 30, 2009

(65) Prior Publication Data

US 2010/0124763 A1 May 20, 2010

Related U.S. Application Data

(60) Provisional application No. 61/110,187, filed on Oct. 31, 2008.

(51) Int. Cl.
| | |
|---|---|
| C12Q 1/00 | (2006.01) |
| C12Q 1/04 | (2006.01) |
| G01N 21/65 | (2006.01) |
| G01N 33/68 | (2006.01) |
| G01N 21/35 | (2014.01) |
| G01N 21/3581 | (2014.01) |
| G01N 21/47 | (2006.01) |
| G01N 21/64 | (2006.01) |
| G01N 21/3577 | (2014.01) |

(52) U.S. Cl.
CPC .............. *C12Q 1/04* (2013.01); *G01N 21/65* (2013.01); *G01N 33/6848* (2013.01); *G01N 21/35* (2013.01); *G01N 21/3577* (2013.01); *G01N 21/3581* (2013.01); *G01N 21/47* (2013.01); *G01N 21/64* (2013.01)

(58) Field of Classification Search
CPC ......... H01L 2924/00; H01L 2924/0014; H01L 2924/12042; H01L 2224/32225; H01L 2224/00012; H01L 2224/16225; H01L 2224/73204; H01L 2224/83192; H01L 2224/27312; H01L 2224/2919; H01L 2224/32052; H01L 2224/83104; H01L 2224/0401; H01L 2224/16238; H01L 2224/743; H01L 2224/92125; H01L 21/563; H01L 24/32; H01L 24/83; C12Q 1/04; G01N 21/35; G01N 21/3577; G01N 21/3581; G01N 21/47; G01N 21/64; G01N 21/65; G01N 33/6848; B05B 12/0008; B05B 12/083
See application file for complete search history.

(56) References Cited

U.S. PATENT DOCUMENTS

| | | | |
|---|---|---|---|
| 3,928,139 A | 12/1975 | Dorn | |
| 3,932,222 A | 1/1976 | Dorn | |
| 4,038,150 A | 7/1977 | Dorn et al. | |
| 4,131,512 A | 12/1978 | Dorn | |
| 4,212,948 A | 7/1980 | Dorn | |
| 4,410,630 A | 10/1983 | Zierdt | |
| 4,577,110 A | 3/1986 | MacBride et al. | |
| 4,693,972 A * | 9/1987 | Mansour et al. | 435/34 |
| 4,829,005 A | 5/1989 | Friedman et al. | |
| 4,847,198 A | 7/1989 | Nelson et al. | |
| 5,164,796 A | 11/1992 | DiGuiseppi et al. | |
| 5,474,910 A | 12/1995 | Alfano | |
| 5,770,454 A | 6/1998 | Essenpreis et al. | |
| 5,938,617 A | 8/1999 | Vo-Dinh et al. | |
| 5,948,610 A | 9/1999 | Ho et al. | |
| 6,074,870 A | 6/2000 | Berndt et al. | |
| 6,087,182 A | 7/2000 | Jeng et al. | |
| 6,124,597 A | 9/2000 | Shehada et al. | |
| 6,346,421 B1 | 2/2002 | Anderson et al. | |
| 6,718,077 B1 | 4/2004 | Ferreira et al. | |
| 6,780,602 B2 | 8/2004 | Powers et al. | |
| 6,788,394 B1 | 9/2004 | Garcia-Rubio et al. | |
| 6,794,659 B2 | 9/2004 | Barbieri et al. | |
| 6,834,237 B2 | 12/2004 | Noergaad et al. | |
| 7,027,134 B1 | 4/2006 | Garcia-Rubio et al. | |
| 7,070,739 B1 | 7/2006 | Anderson et al. | |
| 7,186,990 B2 | 3/2007 | Powers | |
| 7,211,377 B1 | 5/2007 | Powers | |
| 8,647,835 B2 * | 2/2014 | Walsh ...................... | C12Q 1/04 435/29 |
| 8,652,800 B2 * | 2/2014 | Walsh ...................... | C12O 1/04 435/29 |
| 9,790,534 B2 * | 10/2017 | Walsh ...................... | C12Q 1/04 |
| 2002/0086289 A1 | 7/2002 | Straus | |
| 2003/0138906 A1 | 7/2003 | Tryland et al. | |
| 2004/0185437 A1 | 9/2004 | Hermet et al. | |
| 2004/0197771 A1 | 10/2004 | Powers et al. | |
| 2004/0197927 A1 | 10/2004 | Jeng et al. | |
| 2005/0070020 A1 | 3/2005 | Klautky et al. | |
| 2005/0273267 A1 | 12/2005 | Maione | |
| 2007/0037135 A1 * | 2/2007 | Barnes ................... | G01N 21/31 435/4 |

(Continued)

FOREIGN PATENT DOCUMENTS

| | | |
|---|---|---|
| WO | WO0221108 | 3/2002 |
| WO | WO2004014322 | 2/2004 |

(Continued)

OTHER PUBLICATIONS

Cleary et al. (Intrinsic properties of bacterial spores and cells, 2002, Cellular and Tissue Engineering, Proceedings of the IEEE-EMBS Special Topics Conference, pp. 139-140).*

(Continued)

*Primary Examiner* — Susan M Hanley

(57) ABSTRACT

The present invention provides a method and system for monitoring, detecting, and/or characterizing a biological particle that may be present in a sample. The method may be accomplished in a sealed container by utilizing a first step time-dependent spectroscopic technique to obtain at least two measurements of a growth composition comprising a sample and correlating said measurements for the detection and/or characterization of a biological particle that may be present in the sample. The method further provides for a subsequent step for the separation, characterizion and/or identification of the microorganisms in the sealed container.

16 Claims, 14 Drawing Sheets

(56) References Cited

U.S. PATENT DOCUMENTS

| | | | |
|---|---|---|---|
| 2007/0111225 | A1 | 5/2007 | Lambert et al. |
| 2007/0175278 | A1 | 8/2007 | Pupples et al. |
| 2007/0269897 | A1 | 11/2007 | Tanaka et al. |
| 2008/0032327 | A1 | 2/2008 | Powers et al. |
| 2008/0259313 | A1 | 10/2008 | Berndt |
| 2008/0297789 | A1 | 12/2008 | Stewart et al. |
| 2009/0156943 | A1 | 6/2009 | Phillips et al. |

FOREIGN PATENT DOCUMENTS

| | | |
|---|---|---|
| WO | WO2005068647 | 7/2005 |
| WO | WO2007030020 | 3/2007 |
| WO | WO2009011585 | 1/2009 |
| WO | WO2009049171 | 4/2009 |
| WO | WO2009100197 | 8/2009 |
| WO | WO2009105061 | 8/2009 |
| WO | WO2009120532 | 10/2009 |

OTHER PUBLICATIONS

Fonseca et al. (Red blood cells inhibit activation-induced cell death and oxidative stress in human peripheral T lymphocytes, 2001, Blood, vol. 97, pp. 3152-3160).*

Yu et al. (Spectroscopic differentiation and quantification of microorganisms in apple juice, 2004, Journal of Food Science, vol. 69, pp. S268-S272).*

Lacey et al. (Identification of transient radical species in microbial systems using diffuse reflectance laser flash photolysis, 2002, Physical Chemistry Chemical Physics, vol. 4, pp. 232-238).*

Lamberg et al. (Detection and quantification of simulated anaerobic bacteremia by centrifugation and filtration, 1983, Journal of Clinical Microbiology, vol. 17, pp. 856-859).*

Alimova et al.; Native Fluorescence Changes Induced by Bactericidal Agents; IEEE Sensors Journal (2005) vol. 5 No. 4 pp. 704-711.

Ammor MS; Recent Advances in the use of Intrinsic Fluorescence for Bacterial Identification and Characterization; J. Fluoresc (2007) vol. 17 pp. 455-459.

Bernhardt et al.; Detection of Bacteria in Blood by Centrifugation and Filtration; J. Clin. Micro. (1991) vol. 29 No. 3 pp. 422-425.

Bhatta et al.; Use of Fluorescence Spectroscopy to Differentiate Yeast and Bacterial Cells; Appl Microbiol Biotechnol (2006) vol. 71 pp. 121-126.

Bronk et al.; Variability of Steady State Bacterial Fluorescence with Respect to Growth Conditions; App. Spectroscopy (1993) vol. 47 No. 4 pp. 436-440.

Dalterio et al.; The Steady-State and Decay Characteristics of Primary Fluorescence From Live Bacteria; App. Spectroscopy (1987) vol. 41 No. 2 pp. 234-241.

Dorn et al.; Blood Culture Technique Based on Centrifugation: Developmental Phase; J. Clin. Micro. (Mar. 1976) vol. 3.

Abstract of Estes et al.; Reagentless Detection of Microorganisms by Intrinsic Fluorescence; Biosens Bioelectron. (2003) vol. 18 No. 5-6 pp. 511-519.

Fukushima et al.; Rapid Separation and Concentration of Food-Borne Pathogens in Food Samples Prior to Quantification by Viable-Cell Counting and Real-Time PCR; App. Envir. Micro. (Jan. 2007) vol. 73 (1) pp. 92-100.

Giana et al.; Rapid Identification of Bacterial Species by Fluorescence Spectroscopy and Classification Through Principal Components Analysis; J. Fluoresc (2003) vol. 13 pp. 489-493.

Gill et al.; Comparison of Lysis-Centrifugation with Lysis-Filtration and a Conventional Unvented Bottle for Blood Culture; J. Clin. Micro. (1984) vol. 20. No. 5 pp. 927-932.

Ginell et al.; Fluorescent Spectrophotometry in the Identification of Bacteria; J. Appl. Bact. (1972) 35(1) pp. 29-36.

Huffman et al.; New method for the detection of micro-organisms in blood: application of quantitative interpretation model to aerobic blood cultures; J. Biom. Optics (May/Jun. 2009) 14(3) pp. 034043-1 through 034043-10.

Jarvis Roger et al.; Surface enhanced Raman Scattering for the Rapid Discrimination of Bacteria; Faraday Discussions Royal Society of Chemistry (Jan. 1, 2006) vol. 132 pp. 281-292.

Kruger et al.; Analysis of the substrate specificity of the *Staphylococcus aureus* sortase transpeptidase SrtA; Biochemistry (Feb. 1, 2004) vol. 43 No. 6 pp. 1541-1551 (Feb. 1, 2004).

Leblanc et al.; Monitoring the identity of bacteria using their intrinsic fluorescence; FEMS Microbiology Letters (2002) 211 pp. 147-153.

Maquelin et al.; Identification of Medically Relevant Microorganisms by Vibrational Spectroscopy; J. Micro. Methods, (Nov. 1, 2002) vol. 51, No. 3, pp. 255-271.

Maquelin et al.; Prospective Study of the Performance of Vibrational Spectroscopies for Rapid Identification of Bacterial and Fungal Pathogens Recovered from Blood Cultures; J. Clin. Micro., (Jan. 1, 2003) vol. 41, No. 1, pp. 324-329.

Abstract of Mason et al.; Taxonomic Identification of Microorganisms by Capture and Intrinsic Fluorescence Detection; Biosens Bioelectron. (2003) vol. 18, No. 5-6, pp. 521-527.

Mothershed et al.; Nucleic acid-based methods for the detection of bacterial pathogens: Present and future considerations for the clinical laboratory; Clinica Chimica Acta, (Jan. 1, 2006) vol. 363, No. 1-2, pp. 206-220.

Neugebauer et al.; Characterization of Bacterial Grwoth and the Influence of UV Resonance Raman Spectroscopy; Biopolymers, (Jul. 2006) vol. 82, No. 4, pp. 306-311.

Pau et al.; A Rapid Enzymatic Procedure for "Fingerprinting" Bacteria by Using Pattern Recognition of Two Dimensional Fluorescence Data; Clin. Chem. (1986) 32/6, pp. 987-991.

Pau et al.; Evaluation of a Forier-Transform-Based Pattern-Recognition Algorithm for Two-Dimensional Fluorescence Data; App. Spectroscopy (1987) vol. 41, No. 3, pp. 496-502.

Popp et al.; Raman-Spectroscopy for a rapid identification of single microorganisms; Proceedings of the Spie—The International Society for Optical Engineering, (2005) vol. 6180, pp. 618024-1.

Abstract of Rativa et al.; Optical Spectroscopy on in vitro Fungal Diagnosos; Conf Proc IEEE Eng Med Biol Soc. (2008) vol. 1, pp. 4871-4874.

Rosch et al.; Fast and reliable identification of microorganisms by means of Raman spectroscopy; Proceedings of the Spie—The International Society for Optical Engineering, (2007) vol. 6622, pp. 66331A-1.

Rubin et al.; Comparison of the Du Pont Isolator 1.5 Microbial Tube and Trypticase Soy Broth for the Recovery of Haemophilus influenzae Type b in Experimental Bacteremia; J. Clin. Micro., (Nov. 1985) vol. 22, No. 5, pp. 815-818.

Sage et al.; Rapid Visual Detection of Microorganisms in Blood Culture; J. Clin. Micro., (Jul. 1984) vol. 20. No. 1, pp. 5-8.

Serebrennikova et al.; Quantitative interpretations of Visible-NIR reflectance spectra of blood; Optics. Society., (Oct. 27, 2008) vol. 16, No. 22, pp. 18215-18229.

Shelly et al.; Characterization of Bacteria by Mixed-Dye Fluorimetry; Clin. Chem. (1983) 29/2, pp. 290-296.

Shelly et al.; Identification of Fluorescent *Pseudomonas* Species; Clin. Chem. (1980) 26/8, pp. 1127-1132.

Sohn et al.; Fluorescence Spectroscopy for Rapid Detection and Characterization of Bacterial Pathogens; App. Spectroscopy (2009) vol. 63, No. 11, pp. 1251-1255.

Sorrell et al.; Bacterial Identification of Otitis Media With Fluorescence Spectroscopy; Lasers in Surgery and Medicine, (1994) vol. 14, pp. 155-163.

Spector et al.; Noninvasive Fluorescent Identification of Bacteria Causing Acute Otitis Media in a Chinchilla Model; Laryngoscope, (2000) vol. 110, pp. 1119-1123.

Warner et al.; Multicomponent Analysis in Clinical Chemistry by Use of Rapid Scanning Fluorescence Spectroscopy; Clin. Chem. (1976) 22/9, pp. 1483-1492.

Zierdt et al.; Development of a Lysis-Filtration Blood Culture Technique; J. Clin. Microbiology, (Jan. 1977) vol. 5, No. 1, pp. 46-50.

International Search Report and Written Opinion of the International Searching Authority for PCT/US2009/005885 dated Feb. 23, 2010.

(56) References Cited

OTHER PUBLICATIONS

Co-pending U.S. Appl. No. 12/460,607 "Method and System for Detection and/or Characterization of a Biological Particle in a Sample", filed Jul. 22, 2009.
Co-pending U.S. Appl. No. 12/589,929 "Methods for Isolation and Identification of Microorganisms", filed Oct. 30, 2009.
Co-pending U.S. Appl. No. 12/589,952 "Methods for Separation, Characterization and/or Identification of Microorganisms using Spectroscopy", filed Oct. 30, 2009.
Co-pending U.S. Appl. No. 12/589,976 "Methods for Separation Characterization and/or Identification of Microorganism using Raman Spectroscopy", filed Oct. 30, 2009.
Co-pending U.S. Appl. No. 12/589,985 "Methods for Separation and Characterization of Microorganisms using Identifier Agents", filed Oct. 30, 2009.
Estes et al.; Reagentless Detection of Microorganisms by Intrinsic Fluorescence; Biosens Bioelectron. (2003) vol. 18 No. 5-6 511-519.
Mason et al.; Taxonomic Identification of Microorganisms by Capture and Intrinsic Fluorescence Detection; Biosens Bioelectron. (2003) vol. 18, No. 5-6, pp. 521-527.
Rativa et al.; Optical Spectroscopy on in vitro Fungal Diagnosos; Conf Proc IEEE Eng Med Biol Soc. (2008) vol. 1, pp. 4871-4874.

\* cited by examiner

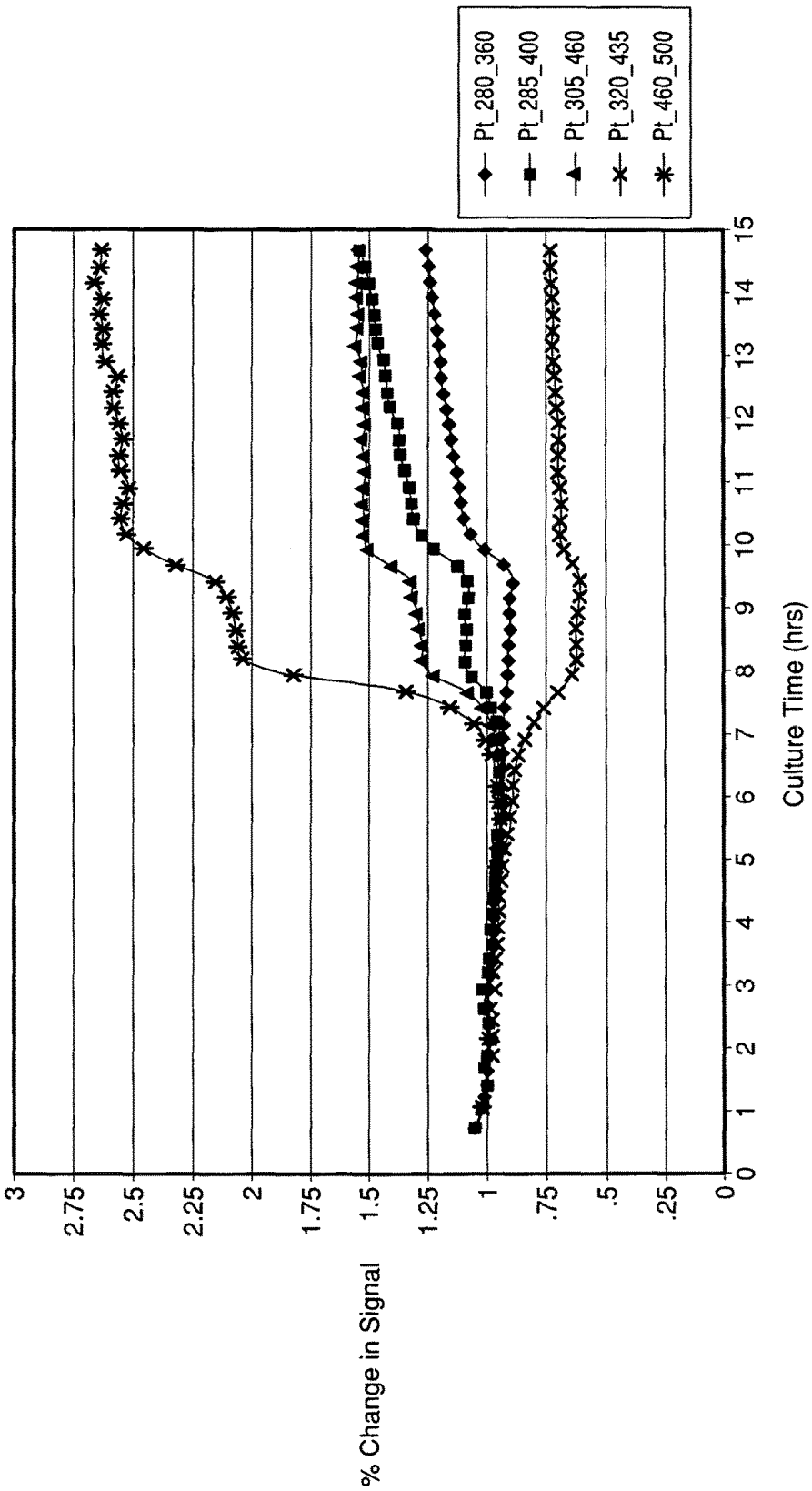

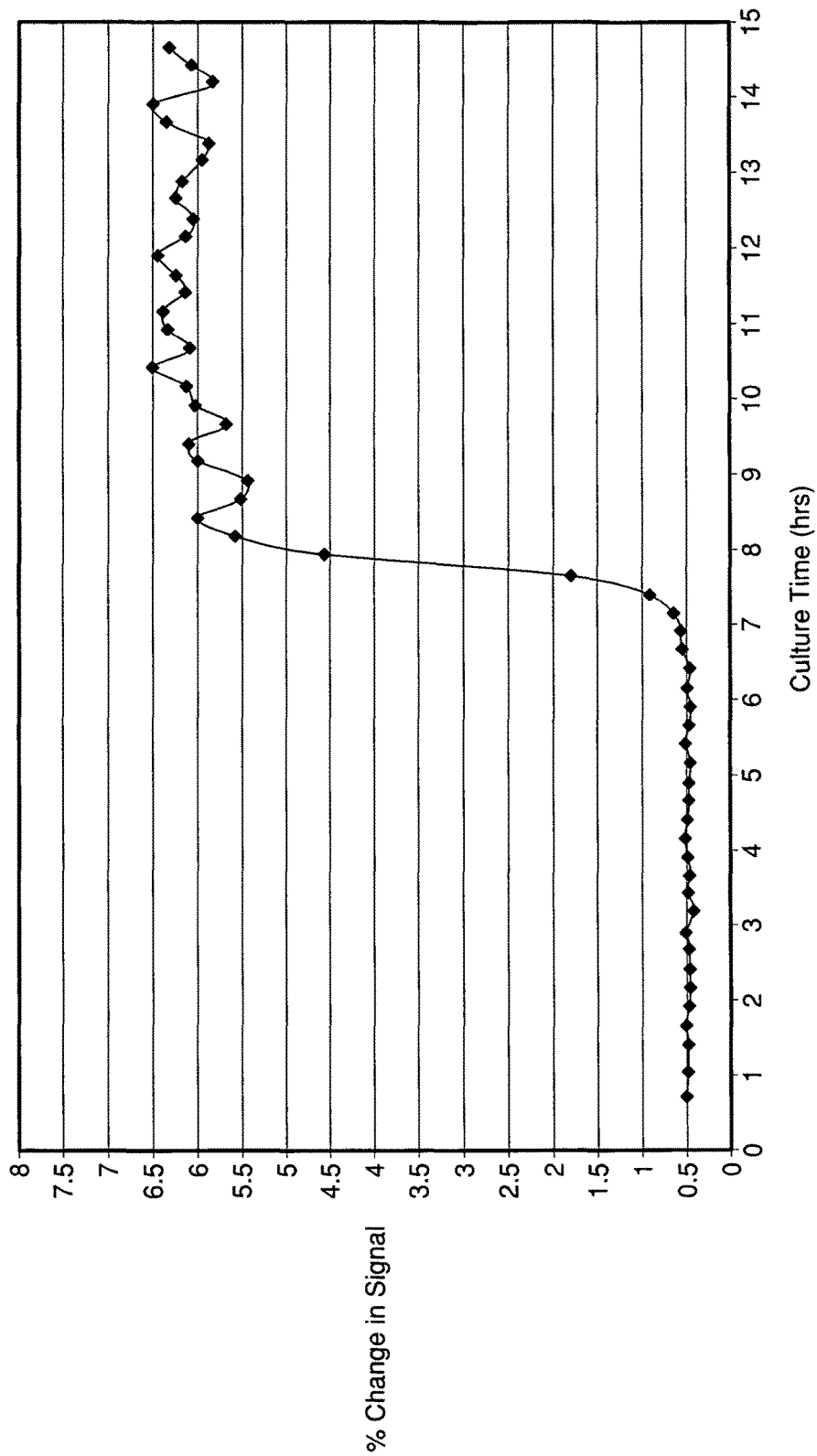

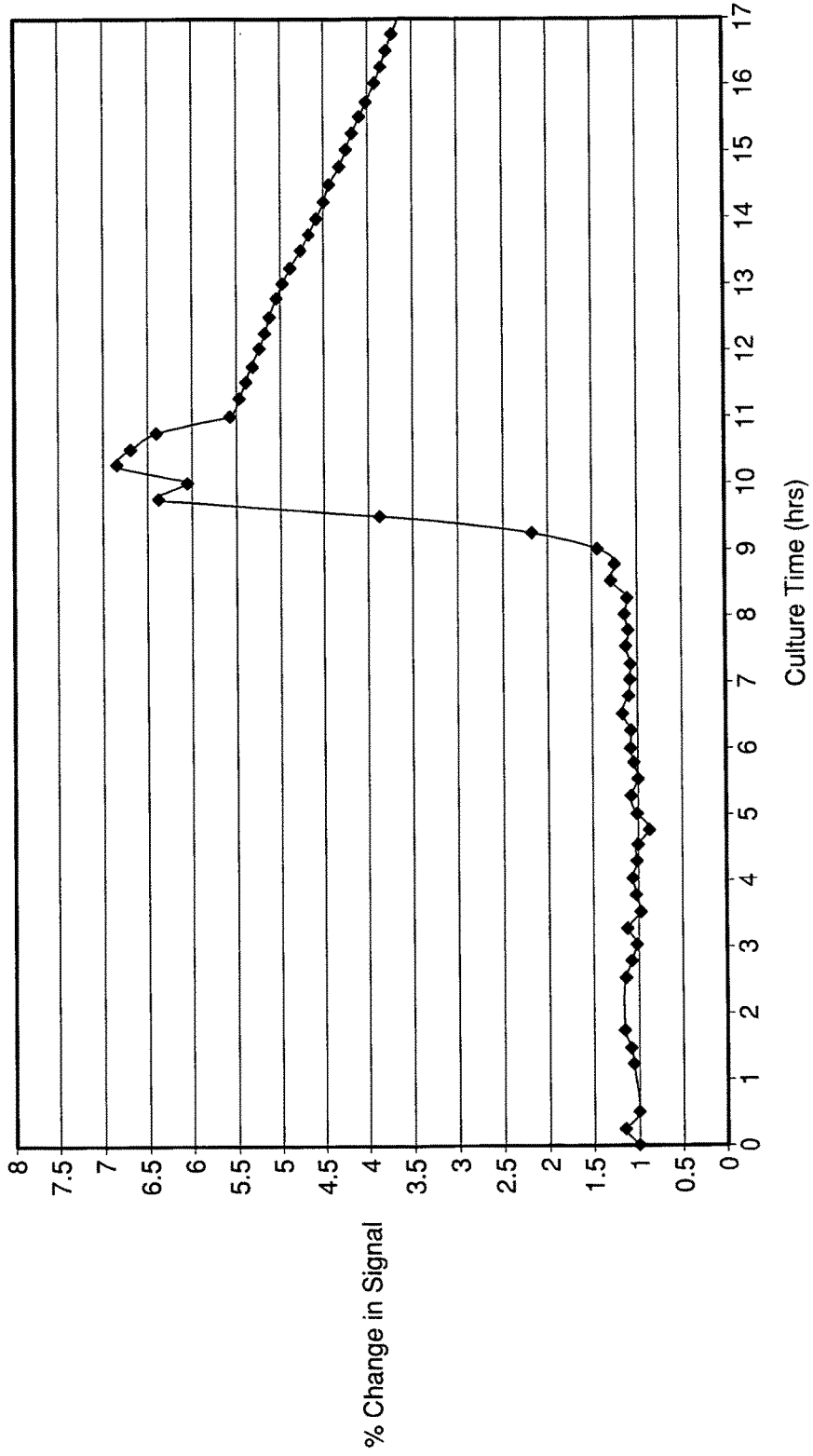

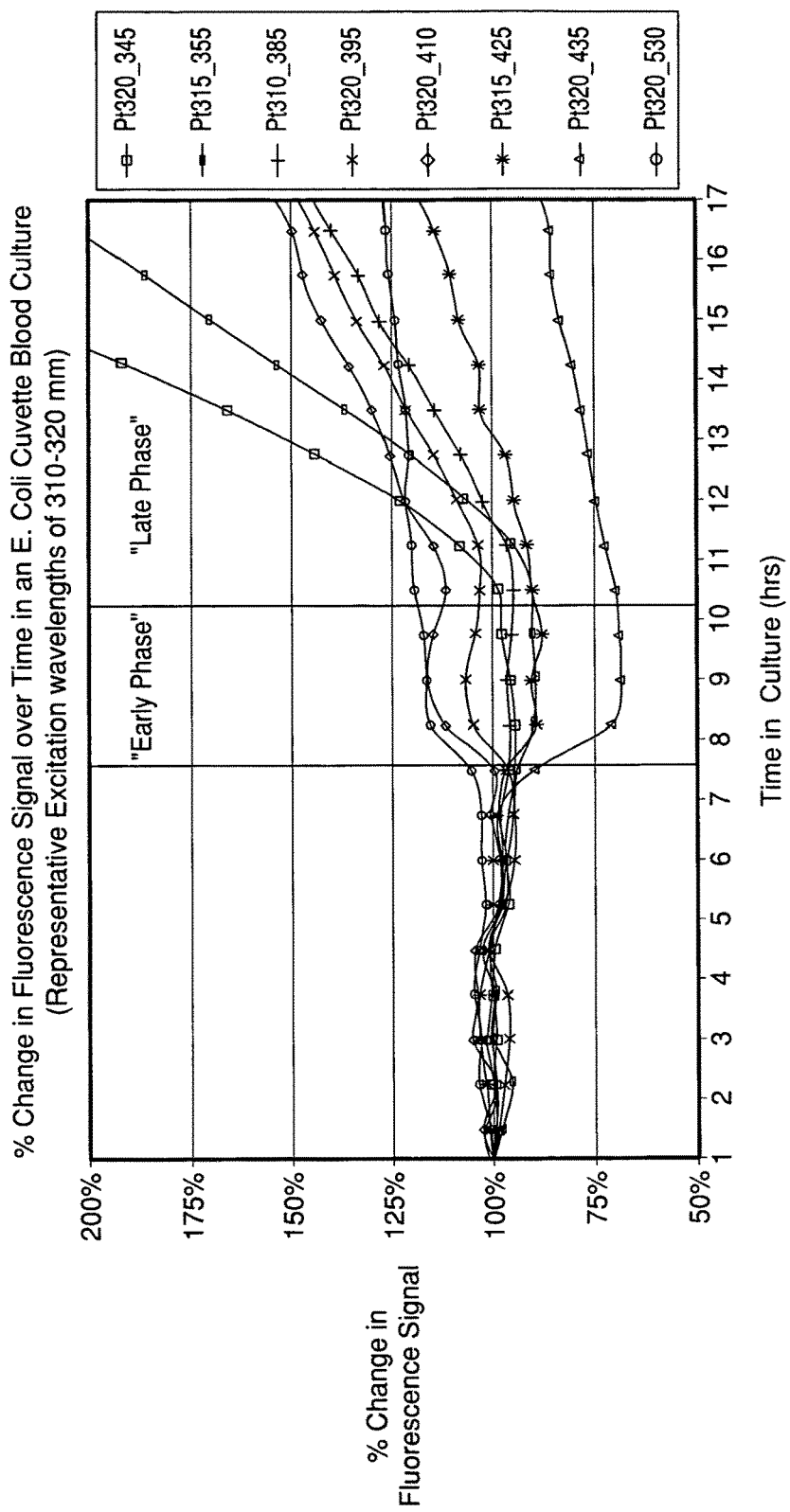

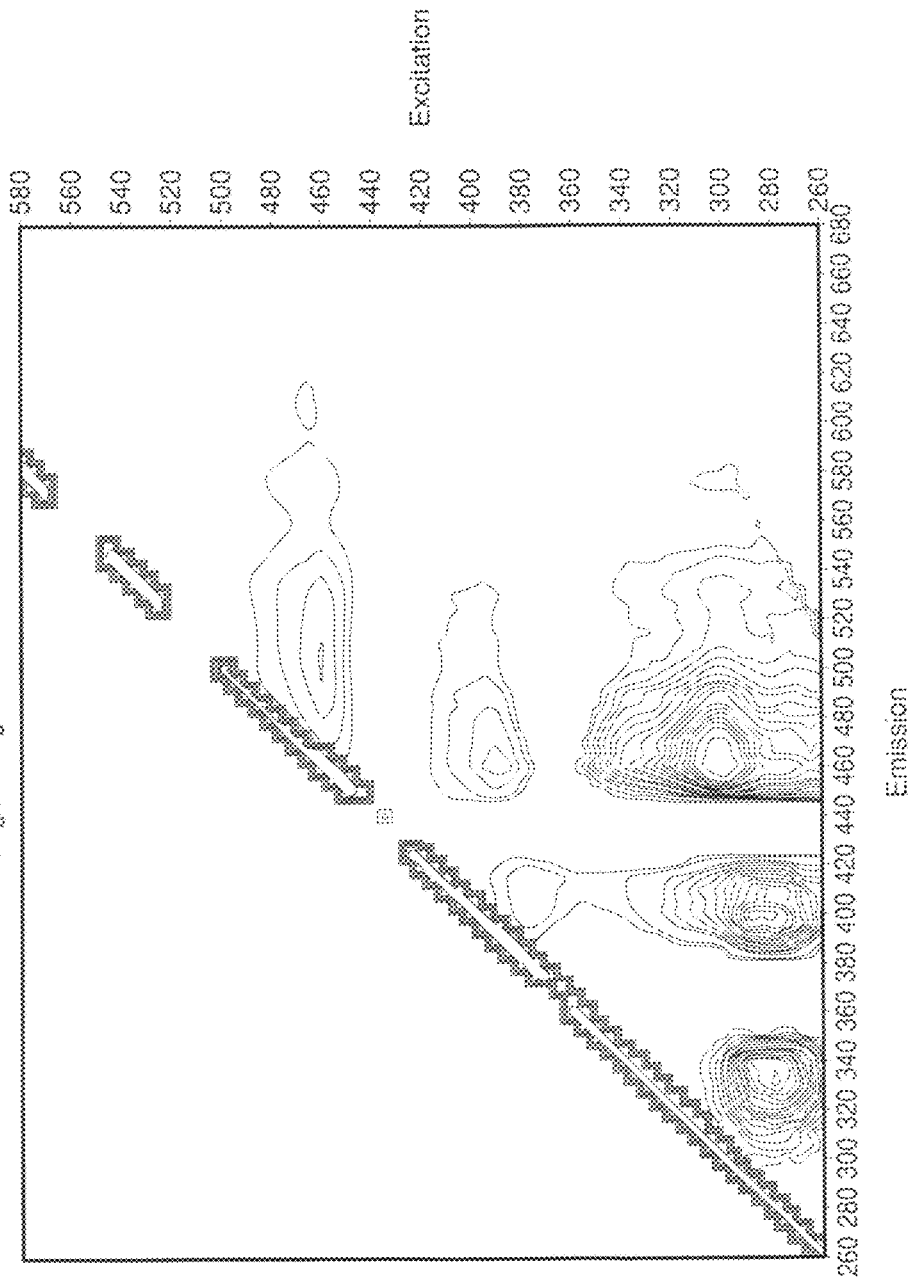

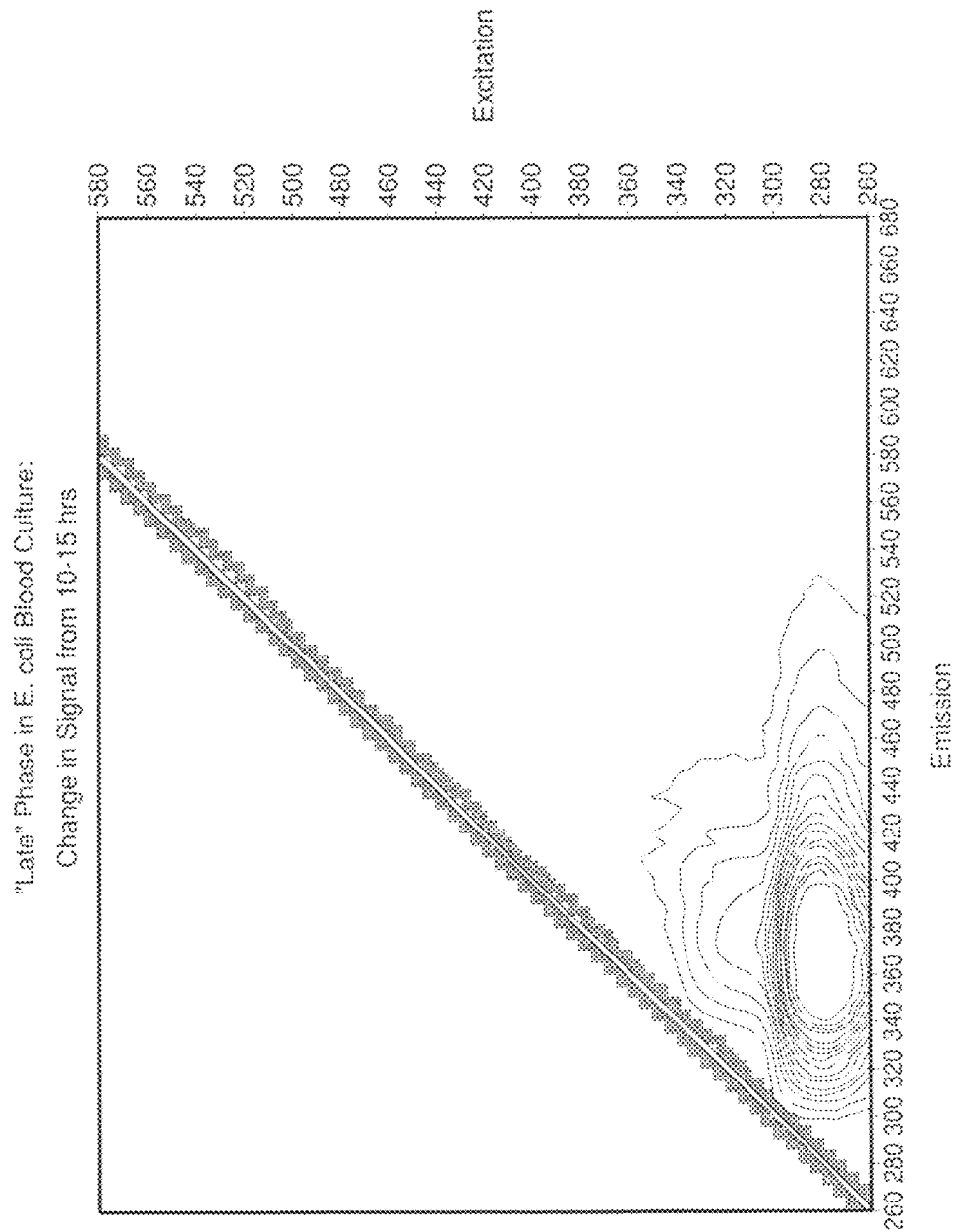

Post-centrifugation of lysed S. aureus-containing blood culture broth

E. coli 103722

C. albicans 304765

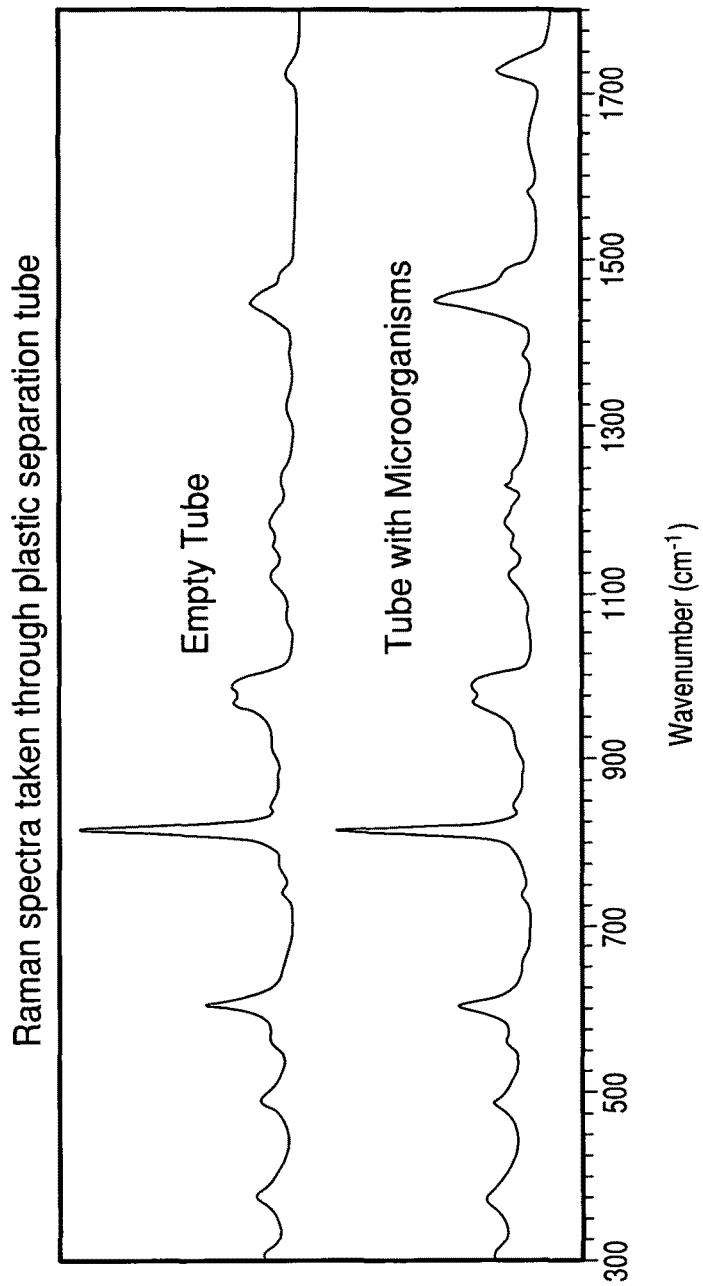

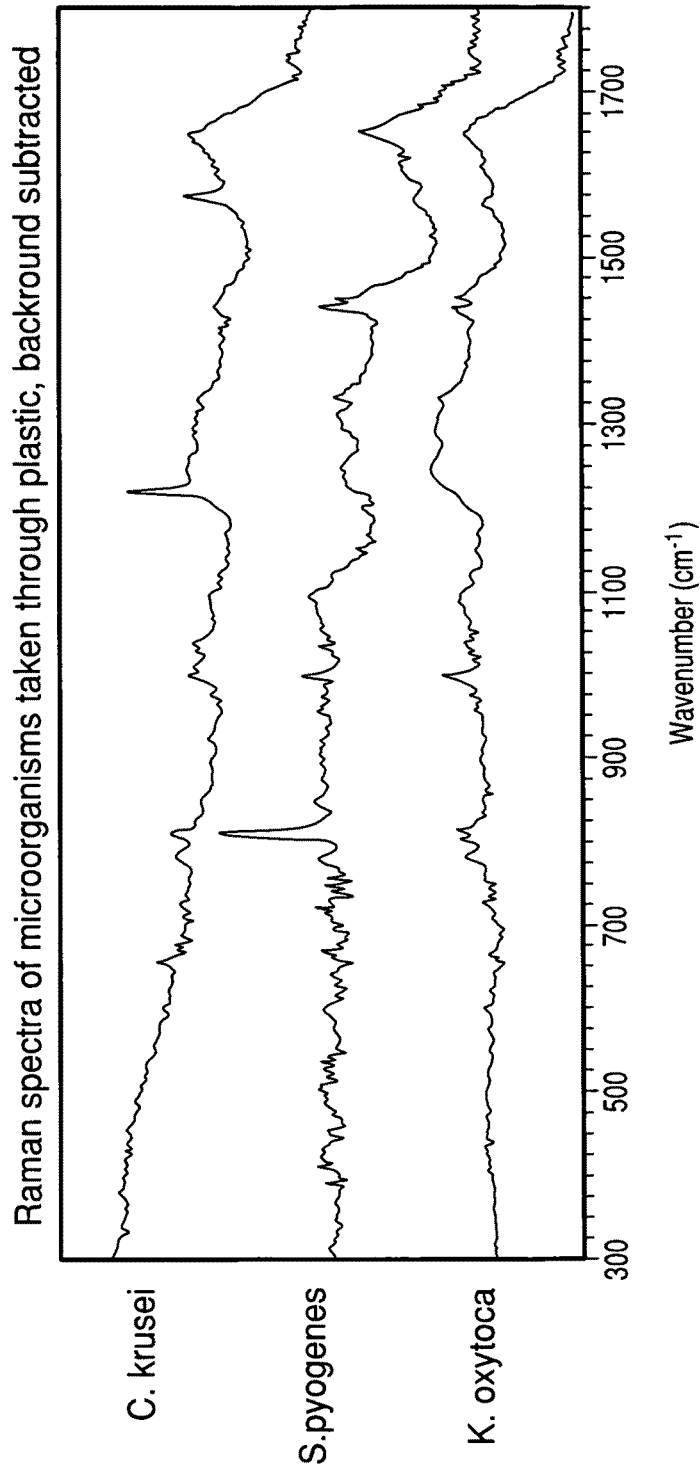

METHOD FOR DETECTION, CHARACTERIZATION AND/OR IDENTIFICATION OF MICROORGANISMS IN A SEALED CONTAINER

CROSS REFERENCE TO RELATED APPLICATION

This application claims the benefit of U.S. Provisional Patent Application No. 61/110,187, entitled, "Method and System for Detection and/or Characterization of a Biological Particle in a Sample", filed Oct. 31, 2008, which is incorporated herein.

FIELD OF THE INVENTION

The present invention relates to methods and systems for detecting, isolating and/or identifying microorganisms in a sample. In particular, the present invention is directed to the detection, characterization and/or identification of microorganisms in a sealed container.

BACKGROUND OF THE INVENTION

The detection of pathogenic microorganisms in biological fluids should be performed in the shortest possible time, in particular in the case of septicemia for which the mortality remains high in spite of the broad range of antibiotics which are available to doctors. The presence of biologically active agents such as a microorganism in a patient's body fluid, especially blood, is generally determined using blood culture bottles. Bloodstream infections are associated with high morbidity and mortality, yet current diagnostic methods, of culture followed by biochemical identification and antibiotic susceptibility testing, can take several days to perform. Typically, empiric therapy is initiated based on clinical symptoms, and test results only impact clinical decisions when the initial therapy fails. The ability to characterize bloodstream infections within the first few hours, preferable within an hour, after a positive blood culture result would significantly boost the clinical relevance of the diagnostic information provided. Molecular amplification methods have been proposed to fill this need, but serious challenges to this approach remain. The positive blood culture broth itself represents a naturally amplified population of microorganisms with potential for use in a variety of rapid, identification (ID) tests.

Traditional automated phenotypic ID tests, such as the Vitek®, Phoenix™ and Microscan® systems, or manual phenotypic tests such as API require that microorganisms be in an appropriate growth phase and free of interfering media and blood products in order to provide robust results. These systems use colonies grown from the positive broth for 18-24 hours on plated media. However, in an effort to obtain faster results, some laboratories have reported using these systems with microorganisms isolated from positive blood culture bottles. These direct-from-the-bottle tests are not appropriate for all microorganisms (e.g., Gram-positive cocci), are not validated by the test manufacturers, and generally take 3-8 hours to provide results. Faster and more broadly specific tests are urgently needed in order to provide the physician with clinically relevant results within the first few hours, preferably within an hour, after a positive culture result.

Optical spectroscopy methods, such as intrinsic fluorescence (IF), infrared spectroscopy (FTIR), or Raman spectroscopy, and mass spectrometry methods such as MALDI-TOF, have the potential to allow for identification of microorganisms very quickly, but may encounter interference from the many highly fluorescent and absorptive compounds present in liquid microbiological culture media and in clinical samples such as blood or combinations thereof. The most commonly employed methods for recovering microorganisms directly from positive blood culture broth are two-step differential centrifugation and centrifugation in a serum separator tube.

Other methods for separation, characterization and/or identification of microorganisms have been described, include:

U.S. Pat. No. 4,847,198 discloses a method for the identification of microorganisms using UV excited Raman spectroscopy. According to the '198 patent, a bacterial suspension is contacted by a single wavelength in the ultra-violet range. A portion of the light energy used is absorbed and a portion of the light energy is emitted. The emitted light energy, resonance enhanced Raman scattering, is measured as backscattered energy. The energy is processed to produce spectra which are characteristic of the bacteria.

U.S. Pat. No. 5,938,617 to Vo-Dinh is directed to a system which identifies biological pathogens in a sample by exciting a sample with light at several wavelengths and synchronously sampling the emission intensities. The system includes mechanisms for exposing the sample to excitation radiation and thereby generating an emission radiation. The biological pathogens may be viruses and bacteria.

U.S. Pat. No. 6,177,266 discloses a method for the chemotaxonomic classification of bacteria with genus, species and strain specific biomarkers generated by matrix assisted laser desorption ionization time-of-flight mass spectrometry (MALDI-TOF-MS) analysis of either cellular protein extracts or whole cells.

In U.S. Pat. No. 7,070,739 a method is presented to extract, separate, and purify microbes including viruses by two-dimensional ultra-centrifuging directly from body fluids or homogenized tissue. In a first centrifuging step, all particles are removed having a sedimentation speed higher than those of the microbes to be identified. In the second ultra-centrifuging step, isopycnic banding is used in liquids filled in to form a wide-range density gradient, using special serrated centrifuge tubes. According to the patent, the separation technique can be used for detecting banded particles by light scatter or fluorescence using nucleic acid specific dyes, and for recovering the banded particles in very small volumes for characterization by mass spectrometry of viral protein subunits and intact viral particles, and by fluorescence flow cytometric determination of both nucleic acid mass and the masses of fragments produced by restriction enzymes.

U.S. Pat. Appl. Pub. No. 2007/0037135 discloses a system for the identification and quantification of a biological sample suspended in a liquid. The system includes a fluorescence excitation module with at least one excitation light source; a sample interface module optically coupled to the fluorescence excitation module for positioning a biological sample to receive excitation light from the at least one excitation light source; a fluorescence emission module optically coupled to the sample interface module and comprising at least one detection device for detecting fluorescence excitation-emission matrices of the biological sample; and a computer module operatively coupled to the fluorescence emission module. The computer module performs multivariate analysis on the fluorescence excitation-emission matrices of the biological sample to identify and quantify the biological sample. However, the '135 application does not discuss identification and quantification of microorganisms from complex biological samples, such as blood.

U.S. Pat. Appl. Pub. No. 2007/0175278 describes using a liquid culture medium for culturing a sample of interest, including for example, blood, urine, feces, intravenous catheters etc., industrial production lines, water systems, a food product, a cosmetic product, a pharmaceutical product and a forensic sample. Subsequently, the microorganisms can be harvested from the liquid medium by methods known in the art, e.g. by centrifugation. The concentrated microorganisms may then be transferred to carrier material, optionally after drying, for obtaining a vibrational spectrum. The patent application discusses various methods for identifying and classifying microorganisms, including vibrational spectroscopy, such as Raman spectroscopy.

However, these methods have several drawbacks. The resultant microbial preparation often contains contaminating red blood cells, platelets, lipid particles, plasma enzymes and cellular debris, which can cause poor results in traditional phenotypic ID tests.

These methods are also very labor-intensive and unsafe due to steps which can result in aerosol exposure of potentially dangerous pathogens to the user. Simple, safe and reliable methods are needed to isolate microorganisms from clinical samples (e.g., blood culture broth) and other complex samples that are free of these interfering materials and compatible with rapid identification technologies.

SUMMARY OF THE INVENTION

The present invention provides methods for detecting, isolating, characterizing and/or identifying microorganisms in a sample. The methods allow for the detection, characterization and/or identification of microorganisms more quickly than prior techniques, resulting in faster diagnoses (e.g., in a subject having or suspected of having septicemia) and identification of contaminated materials (e.g., foodstuffs and pharmaceuticals). The steps involved in the methods of the invention, from detection to characterization and/or identification of microorganisms, can be carried out in a very short time frame to produce clinically relevant actionable information, e.g., in less than about 120 minutes. Additionally, the methods of the invention can be fully automated, thereby reducing the risk of handling infectious materials and/or contaminating samples.

In one aspect the present invention is directed to method for detecting and identifying a microorganism that may be present in a test sample, said method comprising:
(a) inoculating a specimen container comprising a culture medium with said test sample;
(b) detecting growth of said microorganism in said specimen container using a first spectroscopic technique to obtain at least two time-dependent measurements of a growth composition comprising said sample and correlating said measurements to indicate growth of said microorganism in said culture medium;
(c) separating said microorganisms from said culture medium;
(d) interrogating the separated microorganisms in situ to produce measurements which identify the microorganisms; and
(e) identifying said microorganism based on the produced measurements.

In one embodiment, the separation is carried out by layering the test sample over a density cushion in a container and centrifuging the container to pellet the microorganisms while the test sample medium remains on top of the density cushion. In another embodiment, the container has an optical window at the bottom and/or sides so that the microorganism pellet can be interrogated spectroscopically. The microorganisms can be identified by comparing the spectrum of the pellet to a spectrum or spectra of known microorganisms. The ability to identify microorganisms directly in the pellet without further handling enhances the safety features of this method.

In one embodiment, the spectroscopic interrogation is based on intrinsic characteristics of the microorganisms (e.g., intrinsic fluorescence) or the vibrational structure of constituent molecules (e.g., Raman spectroscopy). In other embodiments, the spectroscopic interrogation is based in part on signals obtained from additional agents that are added during the methods of the invention and interact with specific microorganisms or groups of microorganisms.

BRIEF DESCRIPTION OF THE FIGURES

FIGS. 1A and 1B illustrate time-dependent changes in fluorescence signals of seeded blood cultures containing $E.$ $coli$ and $S.$ $aureus$, respectably, at several selected wavelengths.

FIGS. 2A and 2B illustrate time-dependent changes in scattering signals of seeded blood cultures containing $E.$ $coli$ and $S.$ $aureus$, respectably, monitored at an excitation wavelength of 465 and emission wavelength of 465 nm (Ex465/Em465).

FIG. 3 illustrates the percent change in fluorescence signal over time in an $E.$ $Coli$ seeded blood culture with excitation wavelengths of 310-320 nm and emission wavelengths of 345-530 nm.

FIGS. 4A and 4B illustrate the Excitation-Emission Matrix (EEM) measurements data obtained from monitoring the fluorescence of an $E.$ $coli$ seeded blood culture, and demonstration of "Early" phase data (FIG. 4A) and "Late" phase data (FIG. 4B), respectively.

FIG. 10 shows the Raman spectra of various microorganisms processed and recovered from blood culture.

FIG. 11 shows the Raman spectra of 13 $S.$ $aureus$ isolates recovered directly from blood culture broth.

DETAILED DESCRIPTION OF THE INVENTION

Figure 1B:
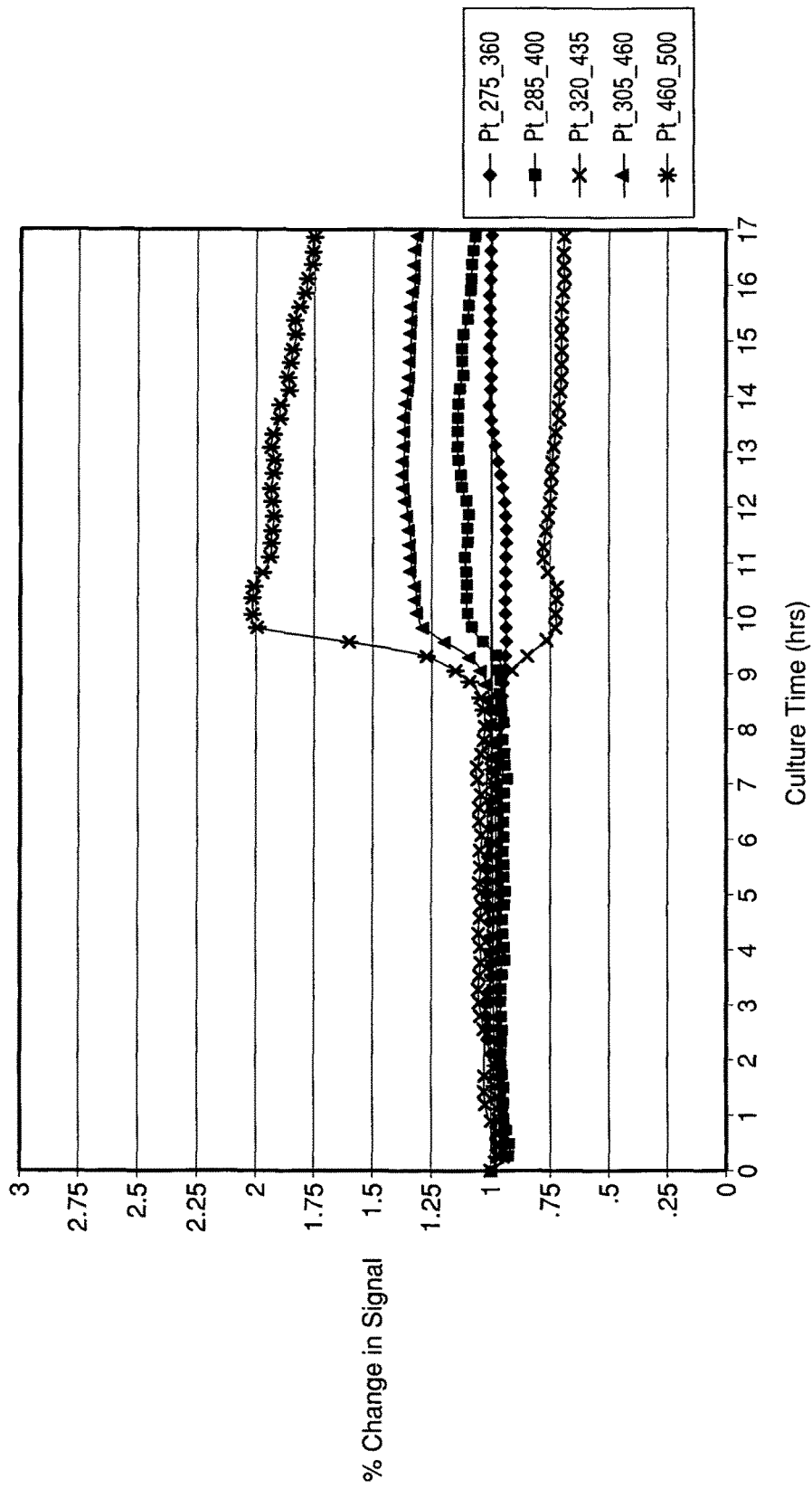

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Definitions.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "microorganism" is intended to encompass organisms that are generally unicellular, which can be multiplied and handled in the laboratory, including but not limited to, Gram-positive or Gram-negative bacteria, yeasts, molds, parasites, and mollicutes. Non-limiting examples of Gram-negative bacteria of this invention include bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia,* and *Legionella.* Non-limiting examples of Gram-positive bacteria of this invention include bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus, Mycobacteria* and *Corynebacteria.* Non-limiting examples of yeasts and molds of this invention include those of the following genera: *Candida, Cryptococcus, Nocardia, Penicillium, Alternaria, Rhodotorula, Aspergillus, Fusarium, Saccharomyces* and *Trichosporon.* Non-limiting examples of parasites of this invention include those of the following genera: *Trypanosoma, Babesia, Leishmania, Plasmodium, Wucheria, Brugia, Onchocerca,* and *Naegleria.* Non-limiting examples of mollicutes of this invention include those of the following genera: *Mycoplasma* and *Ureaplasma.*

In one embodiment, as described in further detail herein, microorganisms from a sample or growth medium can be separated and interrogated to characterize and/or identify the microorganism present in the sample. As used herein, the term "separate" is intended to encompass any sample of microorganisms that has been removed, concentrated or otherwise set apart from its original state, or from a growth or culture medium. For example, in accordance with this invention, microorganisms may be separated away (e.g., as a separated sample) from non-microorganism or non-microorganism components that may otherwise interfere with characterization and/or identification. The term may include a layer of microorganisms sandwiched between two other layers, e.g., microorganisms collected on top of a high-density cushion after centrifugation, or a layer of microorganisms collected on a solid surface (e.g., a filter membrane). The term may also include a collection of microorganisms that has passed partially through a layer (e.g., a density cushion). As such, a separated microorganism sample may include any collection or layer of microorganisms and/or components thereof that is more concentrated than, or otherwise set apart from, the original sample, and can range from a closely packed dense clump of microorganisms to a diffuse layer of microorganisms. Microorganism components that can be comprised in a separated form or sample include, without limitation, pilli, flagella, fimbriae, and capsules in any combination. Non-microorganism components that are separated away from the microorganisms may include non-microorganism cells (e.g., blood cells and/or other tissue cells) and/or any components thereof.

In yet another embodiment, as described in further detail herein, microorganisms from a sample or growth medium can be isolated and interrogated to characterize and/or identify the microorganism present in the sample. As used herein, the term "isolated" is intended to encompass any sample of microorganisms that has been at least partially purified from its original state, or from a growth or culture medium, and any non-microorganisms or non-microorganism components contained therein. For example, in accordance with this invention, microorganisms may be isolated away (e.g., as an isolated sample) from non-microorganisms or non-microorganism components that may otherwise interfere with characterization and/or identification. Non-microorganism components that are separated away from the microorganisms may include non-microorganism cells (e.g., blood cells and/or other tissue cells) and/or any components thereof.

In yet another embodiment, as described in further detail herein, microorganisms from a sample or growth medium can be pelleted and interrogated to characterize and/or identify the microorganism present in the sample. As used herein, the term "pellet" is intended to encompass any sample of microorganisms that has been compressed or deposited into a mass of microorganisms. For example, microorganisms from a sample can be compressed or deposited into a mass at the bottom of a tube by centrifugation, or other known methods in the art. The term includes a collection of microorganisms (and/or components thereof) on the bottom and/or sides of a container following centrifugation. Microorganism components that can be comprised in a pellet include, without limitation, pilli, flagella, fimbriae, and capsules in any combination. In accordance with this invention, microorganisms may be pelleted away (e.g., as a substantially purified microorganism pellet) from non-microorganism or non-microorganism components that may otherwise interfere with characterization and/or identification. Non-microorganism components that are separated away from the microorganisms may include non-microorganism cells (e.g., blood cells and/or other tissue cells) and/or any components thereof.

As used herein, the term "density cushion" refers to a solution having a homogenous density throughout.

The present invention provides a method for monitoring, detecting, characterizing and/or identifying a microorganism that may be present in a test sample. Moreover, the method may be useful for the detection, separation, characterization and/or identification of microorganisms from complex samples such as blood-containing culture media. In accordance with this invention, the multi-step method of the present invention can be carried out in a sealed container.

The method is particularly useful for monitoring, detecting and/or characterizing microorganisms in complex sample types.

The first step of the multi-step method provides for detecting and/or monitoring microorganism growth in a culture medium comprising a first spectroscopic interrogation step to obtain at least two time-dependent measurements of a growth composition comprising the test sample and correlating said measurements to detecting and/or monitoring a microorganism, if present in the sample. The measurements take into account changes in said growth composition as well as detecting and/or characterizing the mass of said microorganism or components thereof.

The second step of the method provides for isolating, characterizing and/or identifying microorganisms from a culture medium detected positive for microorganism growth in the first step. This second step for isolating, characterization and/or identifying a microorganism further involves an optional lysis step, a separation step for separation, isolation or pelleting of the microorganism, and a second interrogation step to obtain data useful for the characterization and/or identification of the microorganism.

The rapid methods allow for the detection, characterization and/or identification of microorganisms more quickly than prior techniques, resulting in faster diagnoses (e.g., in a subject having or suspected of having septicemia) and detection, characterization, and/or identification of contaminated materials (e.g., foodstuffs and pharmaceuticals).

Samples

Samples that may be tested (i.e., a test sample) by the methods of the invention include both clinical and non-clinical samples in which microorganism presence and/or growth is or may be suspected, as well as samples of materials that are routinely or occasionally tested for the presence of microorganisms. The amount of sample utilized may vary greatly due to the versatility and/or sensitivity of the method. Sample preparation can be carried out by any number of techniques known to those skilled in the art although one of the advantages of the present invention is that complex sample types, such as, e.g., blood, bodily fluids, and/or other opaque substances, may be tested directly utilizing the system with little or no extensive pretreatment. In one embodiment, the sample is taken from a culture. In another embodiment, the sample is taken from a microbiological culture (e.g., a blood culture). In another embodiment, the sample is suspected of, or known to, contain microorganisms therein.

Clinical samples that may be tested include any type of sample typically tested in clinical or research laboratories, including, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. In another embodiment, the clinical sample can be cultured, and a culture sample used.

The present invention finds use in research as well as veterinary and medical applications. Suitable subjects from which clinical samples can be obtained are generally mammalian subjects, but can be any animal. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects. Subjects from which samples can be obtained include, without limitation, mammals, birds, reptiles, amphibians, and fish.

Non-clinical samples that may be tested also include substances, encompassing, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. The method is also particularly well suited for real-time testing to monitor contamination levels, process control, quality control, and the like in industrial settings. In another embodiment, the non-clinical sample can be cultured, and a culture sample used.

In one embodiment of the invention, samples are obtained from a subject (e.g., a patient) having or suspected of having a microbial infection. In one embodiment, the subject has or is suspected of having septicemia, e.g., bacteremia or fungemia. The sample may be a blood sample directly from the subject.

Monitoring and/or Detecting Microorganism Growth

In accordance with the first step of the present invention, detection encompasses the observation of at least one change in a sample, as determined by at least two, time-dependent measurements, which may be correlated with the presence of a microorganism in the test sample. Detection may occur almost immediately depending upon a number of factors including the growth rate of the microorganism, fertility of the growth composition, the selectivity of the detection algorithm, and/or the time interval of measurement, and so on. Although the actual detection times may vary depending upon these factors, preferred embodiments may provide detection of microorganisms within about 48 hours from the initiation of the method, more preferably within about 24 hours from the initiation of the method, still more preferably within the range of from about 1 hour to about 16 hours from the initiation of the method, and most preferably within the range of from about 1 hour to about 10 hours from the initiation of the method. In some embodiments, the first spectroscopic interrogation step may provide measurements useful for characterization of the microorganisms present in the test sample, as described in more detail herein and in co-assigned U.S. patent application Ser. No. 12/460,607, titled "Method and System for Detection and/or Characterization of a Biological Particle in a Sample", filed Jul. 22, 2009.

According to the present invention, a test sample is combined with a growth composition which is defined as a composition that maintains the viability and/or the growth of the microorganisms and the combination is subjected to conditions to promote and/pr enhance growth. Typically, the growth composition may comprise sufficient nutrients to promote rapid growth of the microorganisms thereby facilitating earlier detection and characterization, as is well known in the art. For example, growth compositions may comprise media (including agar), liquid culture media (ideal for many uses), or liquid suspension, and the like. Preferably, for microorganism testing, the composition comprises media, such as tryptic soy broth, brain heart infusion broth, Columbia broth and *Brucella* broth, as well as other general purpose complex media known to those skilled in the art, and may include the addition of blood substitutes and specific growth factors. Additionally, ready-to-use specially formulated aerobic and anaerobic culture media for the cultivation of a variety of microorganisms may be incorporated into the system per the requirements of the organisms of interest. Standard blood culture media is preferred for more generalized testing, with the fertility of the media and selectivity of the media adjusted as within the skill of those familiar with the art. Compositions whereby the microorganisms grow in a non-homogenous or particulate manner (e.g. *Mycobacteria,* molds) may also be employed.

In a preferred embodiment, the method includes the use of a sealed container comprising a growth chamber having a test sample and growth composition contained therein. Optionally, the container may be agitated to promote and/or enhance microorganism growth therein, as is known in the art. Typically, the container may be constructed from any material that does not interfere with the growth of the microorganism and does not interfere with the interrogation means of the present invention. More particularly, the container may be constructed from a material that has good transmission characteristics in the UV, visible and/or infrared region of electromagnetic spectrum, with the transmission characteristics present in at least the region where the measurement occurs. For example, the material may include any UV-VIS-IR transparent material, such as glass or plastic, and ideally will have low gas permeability. The material may be single or multi-layer, where preferably at least one layer has low gas permeability. The sealed container may include other desired features within such as a temperature sensor, carbon dioxide sensor, oxygen sensor, colorimetric sensors, combinations thereof, and the like. For example, in some embodiments, the container may have a sensor, preferably an indwelling sensor, to monitor the temperature of the container that may be electronic or optical in nature and provide bottle temperature readings while requiring no physical contact to the container. In another embodiment, the container may also be designed to facilitate sampling once adequate microbial growth occurs so that the microorganisms may be isolated and purified for use in an ID, AST, molecular or other diagnostic test system at any time during monitoring. The container may also have an optical surface or coating for collection of interrogation measurements (e.g., fluorescence and scattered light measurements) using a first interrogation step. Additionally, the container may incorporate a calibration reference and/or an optical reference in different formats, as known to those skilled in the art. For example, the calibration may be accomplished with a feature optically embedded with the optical reference present in an inner layer or coating.

According to the present invention, by monitoring the test sample and growth composition in a time-dependent manner (i.e., by taking at least two time-dependent measurements), the current invention may detect microorganism growth by measuring multiple changes in the surrounding highly fluorescent environment, and classify microorganisms by continuing to monitor changes until characteristic patterns are recorded and analyzed. More particularly, the method is useful in the area of microorganism detection and/or characterization because microorganisms contain, or are composed of molecules that fluoresce naturally, depending on specific cell composition and metabolism. The resultant patterns differ by organism type and thus provide a fingerprint per organism type.

Once detection occurs, or once the sample has been identified as having microorganisms present, it has been found that measurable differences can form the basis of a method for characterization early in the growth phase, sometimes almost instantaneous. Characterization patterns may emerge rapidly after the initial detection, depending upon multiple factors including sample type, sample concentration, organism concentration in sample, type of growth composition, growth rate of the organism, time interval of measurements, and so on. An automated signal may be provided in the system to notify the user upon the characterization of the microorganism, once the microorganism has been characterized into one or more characterization groups (as described herein) or identified by species, etc. In one preferred embodiment, the method automatically detects and characterizes microorganisms present within a complex, highly fluorescent and/or optically dense sample, with characterization specific to at least the level of information provided by a standard Gram stain in the case of bacteria and yeasts. Classification information may be extracted at any point during the growth of the microorganisms once the sample is introduced into the system.

Preferably characterization occurs within about 48 hours of initial detection, more preferably within about 24 hours of initial detection, still more preferably within about 0 to about 16 hours of initial detection, and most preferably within from about 0 to about 8 hours post initial detection. For example, characterization may begin to occur in "early phase" (change occurring from about 0 to about 2 hours post initial detection or positive growth signal) and/or "late phase" (change occurring from about 2 to about 8 hours post initial detection or positive growth signal). Early phase tends to show patterns where spectra are dominated by changes in the growth composition. Late phase typically shows patterns where spectra are dominated by the microorganism mass rather than by changes in the growth composition.

The length of time in which monitoring the sample may occur may vary widely according to the needs of the user. For example, testing may occur for a period of time between testing initiation to days or even months, depending upon the microorganism of interest, etc., as known to those skilled in the art.

When monitoring for microorganism growth the sample may be excited as frequently as the user finds helpful for the particular testing needs, and may be automated by software. For example, for typical microorganism monitoring in blood or body fluid testing, the sample may be excited constantly or periodically. More particularly, the frequency of exciting the sample may be adjusted anywhere from constant excitation to excitation every few hours or every few days or so, more preferably within the range of exciting the sample every minute or so to every three hours, and most preferably within the range of from about every five minutes to about every hour. As used herein, excitation and illumination are used interchangeably.

In the practice of the first spectroscopic interrogation step of the present invention, the sample illumination source, or excitation source, may be selected from any number of suitable light sources as known to those skilled in the art. More preferably, light sources capable of emission in the ultraviolet, visible and near-infrared portions of the electromagnetic spectrum are utilized and are known to those skilled in the art. For example, light sources may be continuum lamps such as a deuterium or xenon arc lamp for generation of ultraviolet light and a tungsten halogen lamp for generation of visible/near-infrared excitation. These light sources provide a broad range of emission, and the spectral bandwidth for specific excitation wavelengths may be reduced using optical interference filters, prisms or optical gratings.

Alternatively, a plurality of narrowband light sources, such as light emitting diodes or lasers, may be spatially multiplexed to provide a multi-wavelength excitation source. For example, currently, light emitting diodes are available from 240 nm to in excess of 900 nm and the sources have a spectral bandwidth of 20-40 nm (full width at half maximum). Lasers are available in discrete wavelengths from the ultraviolet to the near-infrared; many multiplexing methods are known to those skilled in the art.

The spectral selectivity of any of the light sources may be improved by using spectral discrimination means such as a scanning monochromator. Other methods of discrimination may be utilized by persons skilled in the art such as an acousto-optic tunable filter, liquid crystal tunable filter, an array of optical interference filters, prism spectrograph, etc. A consideration in selecting the spectral discriminator takes into account the range of tunability as well as the level of selectivity. By way of illustration, for example, a discriminator might utilize the wavelength range of 300-800 nm with a selectivity of 10 nm. These parameters generally determine the optimum technology necessary to achieve the tunability range as well as the selectivity.

Typically, the light source results in the excitation of the sample followed by measurement of the emission of fluorescence of the sample at predetermined time points or continuously. Similarly, the reflected light (i.e., scattered light) from the excitation source's interaction with the sample may be measured and has been shown to provide pertinent data for detection and characterization.

The emission from the sample may be measured by any suitable means of spectral discrimination, most preferably employing a spectrometer. The spectrometer may be a scanning monochromator that detects specific emission wavelengths whereby the output from the monochromator is detected by a photomultiplier tube or the spectrometer may be configured as an imaging spectrograph whereby the output is detected by an imaging detector array such as a charge-coupled device (CCD) detector array. Other methods of discrimination may be utilized by persons skilled in the art such as an acousto-optic tunable filter, liquid crystal tunable filter, an array of optical interference filters, prism spectrograph, etc. In a preferred embodiment, a discriminator allows the observation of the fluorescence and/or scattering signal by a photodetection means (such as a photomultiplier tube, avalanche photodiode, charge coupled device (CCD) detector array, or electron multiplying charge coupled device (EMCCD) detector array).

The time-dependent spectroscopic technique is used to obtain at least two measurements that are preferably provided as Excitation-Emission Matrix (EEM) measurements. As used herein, EEM is defined as the luminescent spectral emission intensity of fluorescent substances as a function of both excitation and emission wavelength, and may include a full spectrum or a subset thereof, wherein a subset may contain a single or multiple excitation/emission pairs(s). FIGS. 4A and B show contour plots of time-dependent changes over the entire EEM spectra. Additionally, a cross section of the EEM with a fixed excitation wavelength may be used to show the emission spectra for a specific excitation wavelength, and a cross section of the EEM with a fixed emission wavelength may be used to show the excitation spectra for a sample. In one embodiment, multiple EEMs are measured at discrete points in time and using specific excitation-emission wavelength pairs.

In accordance with one embodiment, it has been found that front-face fluorescence spectroscopy provides an advantage in measuring the fluorescence and reflectance properties of highly scattering and highly quenching samples. The front-face method is particularly useful spectroscopic method because it has been found that this configuration is less affected by the interfering components of blood and microbiological culture media. In accordance with this embodiment, the optical surface of the container may be illuminated at such an angle as to provide acceptable results as known to those skilled in the art, (e.g., Eisinger, J., and J. Flores, 1983, "Front-face fluorometry of liquid samples," *Anal. Biochem.* 94:15-21). Preferably, the system is designed such that the spectroscopy measures diffuse reflected light at a minimum of one fixed angle in addition to measuring emitted fluorescence at a minimum of one fixed angle.

According to the invention, control measurements (e.g., fluorescence and/or reflectance measurements) are taken for known microorganisms in specific sample types thus allowing for correlation of measured test data with characterization of the microorganisms of interest using various mathematical methods known to those skilled in the art. For example, the data from samples may be compared with the baseline or control measurements utilizing software systems known to one skilled in the art. More particularly, the fluorescence and scattering data may be analyzed by a number of multivariate analysis methods, such as, for example, General Discriminant Analysis (GDA), Partial Least Squares Discriminant Analysis (PLSDA), Partial Least Squares regression, Principal Component Analysis (PCA), Parallel Factor Analysis (PARAFAC), Neural Network Analysis (NNA) and Support Vector Machine (SVM). These methods may be used to classify unknown microorganisms of interest (preferably a select group of microorganisms) into relevant groups based on existing nomenclature, or into naturally occurring groups based on the organism's metabolism, pathogenicity and virulence in designing the system for monitoring, detecting and/or characterizing the organism as described previously.

In a preferred embodiment, the system detects microorganisms using change in intrinsic fluorescence and/or reflectance of the culture media and sample, taking into account the growth of the microorganism itself and the changes in the kinetics due to metabolism of the microorganism in the culture. The intrinsic fluorescence or auto fluorescence of the microorganism, particularly bacteria, leverages the fact that the bacteria contain natural fluorophores such as aromatic amino acids (e.g., tryptophan, tyrosine, phenylalanine) that can be excited via a multi-wavelength light source.

The container used in the system to hold the sample may further comprise a combined $CO_2$ or other sensor that may be included for any number of reasons, including, but not limited to, compatibility with previous systems; contamination detection during manufacturing, transport or storage; and accommodation of delayed entry of bottles into an incubation/reading system. Still further, the container may have included a radio frequency identification device, barcode, or the like to store data from an initial read of the bottle at time of sample collection (including time), information from a test (could be used for post characterization), manufacturing information (lot, date, expiration, initial readings, etc.), patient and sample information at time acquired at the time of collecting the sample, and the like.

As previously discussed herein, a growth culture detected positive for the growth of microorganisms can be further processed, in accordance with this invention, for additional characterization and/or identification. For example, a culture medium detected as positive for the growth of microorganisms can subsequently be subjected to methods for the separation, characterization and/or identification of microorganisms disclosed in the following commonly assigned U.S. patent applications: (1) Ser. No. 12/589,929, entitled "Method for the Isolation and Identification of Microorganisms", filed Oct. 30, 2009; (2) Ser. No. 12/589,952, entitled "Method for Separation, Characterization and/or Identification of Microorganisms using Spectroscopy", filed Oct. 30, 2009; (3) Ser. No. 12/589,936, entitled "Method for Separation, Characterization and/or Identification of Microorganisms using Mass Spectrometry", filed Oct. 30, 2009; and (4) Ser. No. 12/589,976, entitled "Method for Separation, Characterization and/or Identification of Microorganisms using Raman Spectroscopy", filed Oct. 30, 2009. These applications are incorporated herein by reference. Briefly, these inventions disclosed methods for isolating, characterizing and/or identifying microorganisms in a sample. The methods allow for the separation, characterization and/or identification of microorganisms more quickly than prior techniques, resulting in faster diagnoses (e.g., in a subject having or suspected of having septicemia) and identification of contaminated materials (e.g., foodstuffs and pharmaceuticals). In these, and other methods of characterizing and/or identifying microorganisms, it is often necessary to provide a separated, isolated, or pelleted microorganism sample for subsequent characterization and/or identification procedures.

Optional Lysis Step

In some embodiments, it may be helpful to selectively lyse non-microorganism cells that may be present in the growth composition prior to the separation and second interrogation step. Non-microorganism cells (e.g., blood cells and/or tissue cells) may be selectively lysed to permit separation of microorganisms from other components of the sample. The separation of microorganisms from other components prevents interference during the second interrogation step. If non-microorganism cells are not expected to be present in the sample or not expected to interfere with the interrogation step, the lysis step may not need to be carried out. In one embodiment, the cells to be lysed are non-microorganism cells that are present in the sample and no microorganism cells that may be present in the sample are lysed. However, in some embodiments, the selective lysing of specific classes of microorganisms may be desirable and thus can be carried out according to the methods described herein and as are well known in the art. For example, a class of undesired microorganisms can be selectively lysed, e.g., yeast are lysed while bacteria are not or vice versa. In another embodiment, the desired microorganisms are lysed in order to separate a particular subcellular component of the microorganisms, e.g., cell membranes or organelles. In one embodiment, all of the non-microbial cells are lysed. In other embodiments, a portion of the non-microbial cells are lysed, e.g., enough cells to prevent interference with the interrogation step. The lysing of cells may be carried out by any method known in the art to be effective to selectively lyse cells with or without lysing microorganisms, including, without limitation, addition of a lysis solution, sonication, osmotic shock, chemical treatment, and/or a combination thereof.

A lysis solution is one that is capable of lysing cells, e.g., non-microorganism cells (e.g., by solubilizing eukaryotic cell membranes) and/or microorganism cells. In one embodiment, the lysis solution can comprise one or more detergents, one or more enzymes, or a combination of one or more detergents and one or more enzymes, and can further include additional agents. In one embodiment, the detergent can be a non-denaturing lytic detergent, such as octylphenol ethoxylate (e.g., Triton® X-100 Triton® X-100-R, Triton® X-114), NP-40, Genapol® C-100, Genapol® X-100, (Octylphenoxy)polyethoxyethanol (e.g., Igepal® CA 630, Arlasolve™ 200, polyoxyethylene 10 oleoyl ether (e.g., Brij® 96/97), CHAPS, octyl β-D-glucopyranoside, saponin, and nonaethylene glycol monododecyl ether (C12E9, polidocenol). Optionally, denaturing lytic detergents can be included, such as sodium dodecyl sulfate, N-laurylsarcosine, sodium deoxycholate, bile salts, hexadecyltrimethylammonium bromide, SB3-10, SB3-12, amidosulfobetaine-14, and C7BzO. Optionally, solubilizers can also be included, such as polyoxyethylene (20) oleyl ether (e.g., Brij® 98), ), polyoxyethylene 20 cetyl ether (e.g., Brij® 58), polyoxyethylene (23) lauryl ether (e.g., Brij® 35), polyoxyethylenesorbitan monooleate (e.g., Tween® 80), polyoxyethylene sorbitol ester (e.g., Tween® 20), polyoxyalkylene ether (e.g., Pluronic® L64, Pluronic® P84), non-detergent sulfobetaines (NDSB 201), amphipols (PMAL-C8), and methyl-β-cyclodextrin. Typically, non-denaturing detergents and solubilizers are used at concentrations above their critical micelle concentration (CMC), while denaturing detergents may be added at concentrations below their CMC. For example, non-denaturing lytic detergents can be used at a concentration of about 0.010% to about 10%, e.g., about 0.015% to about 1.0%, e.g., about 0.05% to about 0.5%, e.g., about 0.10% to about 0.30% (final concentration after dilution with the sample). In another embodiment, polyoxyethylene detergent detergents may be preferred. The polyoxyethylene detergent can comprise the structure $C_{12-18}/E_{9-10}$, wherein C12-18 denotes a carbon chain length of from 12 to 18 carbon atoms and E9-10 denotes from 9 to 10 oxyethylene hydrophilic head groups. For example, the polyoxyethylene detergent can be selected from the group consisting of Brij® 97, Brij® 96V, Genapol® C-100, Genapol® X-100, nonaethylene glycol monododecyl ether (polidocanol), or a combination thereof.

Enzymes that can be used in lysis solutions include, without limitation, enzymes that digest nucleic acids and other membrane-fouling materials (e.g., proteinase XXIII, DNase, neuraminidase, polysaccharidase, Glucanex®, and Pectinex®). Other additives that can be used include, without limitation, reducing agents such as 2-mercaptoethanol (2-Me) or dithiothreitol (DTT) and stabilizing agents such as magnesium, pyruvate, and humectants. The lysis solution can be buffered at any pH that is suitable to lyse the desired cells, and will depend on multiple factors, including without limitation, the type of sample, the cells to be lysed, and the detergent used. In some embodiments, the pH can be in a range from about 2 to about 13, e.g., about 6 to about 13, e.g., about 8 to about 13, e.g., about 10 to about 13. Suitable pH buffers include any buffer capable of maintaining a pH in the desired range, e.g., about 0.05 M to about 1.0 M CAPS.

In one embodiment, the lysis solution is added directly to the culture medium after a positive detection for microorganism growth and mixed. The culture medium/lysis solution mixture is then incubated for a sufficient time for lysis and solubilization of cell membranes to occur, e.g., about 1, 2, 3, 4, 5, 10, 15, 20, 25, 30, 40, 50, or 60 seconds, or about 2, 3, 4, 5, 6, 7, 8, 9, 10, 15, or 20 minutes or longer, e.g., about 1 second to about 20 minutes, about 1 second to about 5 minutes, or about 1 second to about 2 minutes. The incubation time will depend on the strength of the lysis solution, e.g., the concentration of the detergent and/or enzymes. In general, milder lysis buffers will require more time and a greater dilution of the sample to fully solubilize non-microbial cells. The strength of the lysis solution can be selected based on the microorganisms known to be or suspected to be in the sample. For microorganisms that are more susceptible to lysis, a mild lysis solution can be used. The lysis can take place at a temperature of about 2° C. to about 45° C., e.g., about 15° C. to about 40° C., e.g., about 30° C. to about 40° C. In one embodiment, the lysis solution can be loaded into a syringe and the sample can then be aspirated into the syringe such that mixing and incubation occurs within the syringe. In one embodiment, the lysis solution can be loaded into a syringe and the sample can then be aspirated into the syringe such that mixing and incubation occurs within the syringe.

In some embodiments, the lysis conditions (e.g., the solution or the incubation time), as well as the separation and/or interrogation steps, can be sufficient to kill some or all of the microorganisms in the sample. The methods of the present invention are highly versatile and do not require that all microorganisms be alive for the isolation and identification to occur. In certain embodiments, some or all of the microorganisms may be dead, with death occurring before, during, and/or after the steps of the methods being carried out.

Separation Step

The next step in the multi-step method of the present invention (e.g., the step after the sample has been lysed, if a lysing step is performed) is a separation step. The separation step can be carried out to separate the microorganisms from other components of the growth composition (e.g., non-microorganisms or components thereof) and to concentrate the microorganisms into an isolated microorganism sample or microorganism pellet that can undergo a second interrogation step for identification and characterization purposes. The separation does not have to be complete, i.e., it is not required that 100% separation occur. All that is required is that the separation of the microorganisms from other components of the sample be sufficient to permit interrogation of the microorganisms without substantial interference from the other components. For example, the separation can result in a microorganism pellet that is at least about 10, 20, 30, 40, 50, 60, 70, 80, 90, 95, 96, 97, 98, or 99% pure or higher.

In one embodiment, the separation is carried out using a density cushion and a centrifugation step. In accordance with this embodiment, a density cushion can be carefully added to the container, typically, as a second or separate liquid phase just below the culture medium/lysis solution micture. The container can then be centrifuged under conditions which allow the microorganisms to be isolated (e.g., the microorganisms can form a pellet at the bottom and/or sides of the container). In accordance with this embodiment, other components of the sample (e.g., non-microorganisms or components thereof that may be present in the sample medium) stay on top of the density cushion or within the top portion of the density cushion. In one embodiment, the density cushion also serves to separate live microorganisms from dead microorganisms (which do not pass through the density cushion). In another embodiment the density cushion does not comprise a density gradient, either before or after the centrifugation. In other words, the separation container is not centrifuged for a sufficient amount of time and/or acceleration for the material making up the density cushion to form a density gradient.

The density of the cushion is selected such that the microorganisms in the sample pass through the cushion while other components of the sample (e.g., blood culture broth, cell debris) remain on top of the cushion or do not pass all of the way through the density cushion. The density cushion may also be selected to separate live microorganisms (which pass through the cushion) from dead microorganisms (which do not pass through the cushion). Suitable densities will depend on the material used in the density cushion and on the sample to be separated. In one embodiment, the density of the cushion is in the range of about 1.025 to about 1.120 g/ml, e.g., about 1.030 to about 1.070 g/ml, about 1.040 to about 1.060 g/ml or any range between about 1.025 to about 1.120 g/ml. In another embodiment, the density of the cushion is about 1.025, 1.030, 1.035, 1.040, 1.045, 1.050, 1.055, 1.060, 1.065, 1.070, 1.075, 1.080, 1.085, 1.090, 1.095, 1.100, 1.105, 1.110, 1.115, or 1.120 g/ml.

The material for the density cushion can be any material that has the appropriate density range for the methods of this invention. In one embodiment, the material is colloidal silica. The colloidal silica may be uncoated (e.g., Ludox® (W.R. Grace, CT)) or coated, e.g., with silane (e.g., PureSperm® (Nidacon Int'l, Sweden) or Isolate® (Irvine Scientific, Santa Ana, Calif.)) or polyvinylpyrrolidone (e.g., Percoll™, Percoll™ Plus (Sigma-Aldrich, St. Louis, Mo.)). In one embodiment, the colloidal silica exhibiting the least interference with spectroscopic interrogation is selected, e.g., the material with the lowest intrinsic fluorescence. The colloidal silica may be diluted in any suitable medium to form the proper density, e.g., balanced salt solutions, physiological saline, and/or 0.25 M sucrose. Suitable densities can be obtained with colloidal silica at a concentration of about 15% to about 80% v/v, e.g., about 20% to about 65% v/v. Another suitable material for density cushions is an iodinated contrast agent, e.g., iohexol (Omnipaque™ NycoPrep™, or Nycodenz®) and iodixanol (Visipaque™ or OptiPrep™). Suitable densities can be obtained with iohexol or iodixanol at a concentration of about 10% to about 25% w/v, e.g., about 14% to about 18% w/v, for blood culture samples. Sucrose can be used as a density cushion at a concentration of about 10% to about 30% w/v e.g., about 15% to about 20% w/v, for blood culture samples. Other suitable materials that can be used to prepare the density cushion include low viscosity, high density oils, such as microscope immersion oil (e.g., Type DF; Cargille Labs, New York), mineral oil (e.g., Drakeol® 5, Draketex 50, Peneteck®; Penreco Co., Pennsylvania), silicone oil (polydimethylsiloxane), fluorosilicone oil, silicone gel, metrizoate-Ficoll® (LymphoPrep™) , e.g., at a concentration of about 75% to about 100% for blood culture samples, diatrizoate-dextran (PolymorphoPrep™), e.g., at a concentration of about 25% to about 50% for blood culture samples, carboxymethyl cellulose, hydroxypropylmethyl cellulose, polyethylene oxide (high molecular weight), polyoxyalkylene ether (e.g., Pluronic® F127, Pluronic® F68), mixtures of Pluronic® compounds, polyacrylic acid, cross-linked polyvinyl alcohol, cross-linked polyvinyl pyrrolidine, PEG methyl ether methacrylate, pectin, agarose, xanthan, gellan, Gellan Gum (e.g., Phytagel™), sorbitol, a sucrose and epichlorohydrin copolymer (Ficoll® (e.g., Ficoll® 400 at a concentration of about 10% to about 15% for blood culture samples), glycerol, dextran (e.g., at a concentration of about 10% to about 15% for blood culture samples), glycogen, cesium chloride (e.g., at a concentration of about 15% to about 25% for blood culture samples), perfluorocarbon fluids (e.g., perfluoro-n-octane), hydrofluorocarbon fluids (e.g., Vertrel XF), and the like as are well known in the art. In one embodiment, the density cushion is selected from one or more of colloidal silica, iodixanol, iohexol, cesium chloride, metrizoate-Ficoll®, diatrizoate-dextran, sucrose, Ficoll® 400, and/or dextran in any combination. The density cushion can also be made up of a combination of materials, e.g., a combination of colloidal silica and oil. Certain combinations of the above compounds may be beneficial for the separation and reading steps of the present invention. For example, combinations of compounds with different UV-quenching properties, such as cesium chloride and iohexol.

The volume/height of the density cushion should be sufficient to achieve separation of the microorganisms from other sample components. For example, a volume of about 1 ml to about 20 ml can be used, e.g., about 2 ml to about 10 ml, e.g., about 3 ml to about 8 ml. The available space in the container for sample will depend on the size and shape of the container.

In one embodiment of the invention, the separation step can be carried out by centrifuging in a swing out rotor so that the microorganisms form a pellet directly on the bottom of the container. The container is centrifuged at a sufficient acceleration and for a sufficient time for the microorganisms to be separated (e.g., a pellet formed) from other components of the sample. The centrifugation acceleration can be about 1,000×g to about 20,000×g, e.g., about 2,000×g to about 15,000×g, e.g., about 4,000×g to about 10,000×g, etc. The centrifugation time can be about 30 seconds to about 30 minutes, e.g., about 1 minute to about 15 minutes, e.g., about 1 minute to about 5 minutes. The centrifugation can be carried out at a temperature of about 2° C. to about 45° C., e.g., about 15° C. to about 40° C., e.g., about 20° C. to about 30° C. In one embodiment, the container comprises a closure, and the closure is applied to the container to form a hermetic seal during its manufacture. The presence of a closure decreases the risks from handling microorganisms that are or may be infectious and/or hazardous, as well as the risk of contaminating the sample. One of the advantages of the methods of the invention is the ability to carry out the steps of the methods (e.g., detection, lysis, separation, interrogation, and/or identification) with the microorganisms in a sealed container (e.g., a hermetically sealed container). The present methods, involving the use of automated systems, avoid the health and safety risks associated with handling of highly virulent microorganisms, such as occurs with recovery of microorganisms from samples for direct testing. In one embodiment, the container is not centrifuged for a sufficient time and/or force for a density gradient to form within the density cushion. The present invention does not involve ultracentrifugation of samples, e.g., centrifugation at forces greater than about 100,000×g. Further, the present invention does not involve isopycnic (equilibrium) sedimentation or banding.

As previously described herein, the sealed container of the present invention may comprise a growth chamber having a test sample and growth composition contained therein. Typically, the container may be constructed from any material that does not interfere with the growth of the microorganism and does not interfere with the interrogation means of the present invention. The sealed container should also have sufficient volume to hold a test sample, a culture medium, a lysis solution, and a density cushion. In one embodiment, the container fits or can be fitted into a centrifuge rotor. The volume of the container can be about 1 ml to about 100 ml, e.g., about 2 ml to about 50 ml, e.g., about 5 ml to about 30 ml. In one embodiment, the sealed container of the present invention may include features useful for the separation, isolation or pelleting of microorganisms. For example, the container may have a wide internal diameter in an upper portion to hold the sample and culture medium. The upper portion of the container will allow for incubation and growth of any microorganisms that may be present in the test sample. The container may also provide enough room for the addition of a density cushion after detection of a positive culture. The container may also provide a lower portion having a narrow internal diameter where the pellet of microorganisms can be interrogated. The narrow portion can have an internal diameter of from about 0.05 to about 0.5 inches, e.g., from about 0.1 to about 0.25 inches. The container may further comprise a tapered internal diameter portion can connect the upper and lower portions. The tapered portion can have an angle of about 20 to about 70 degrees, e.g., about 30 to about 60 degrees. In one embodiment, the lower narrow portion is less than 25% of the total height of the container, e.g., less than about 20%, 10%, or less than 5% of the total height of the container.

In another embodiment, the sealed container can comprise an optical window through which the interrogation can occur. The optical window may be on the bottom, top, and/or sides of the container. The window can be composed of any material that is transparent to light (e.g., at least a portion of the near infrared (NIR; 700 nm-1400 nm), ultraviolet (UV; 190 nm-400 nm) and/or visible (VIS; 400 nm-700 nm) light spectrum). Examples of suitable materials include, without limitation, acrylic, methacrylate, quartz, fused silica, sapphire, and/or a cyclic olefin copolymer (COC). In one embodiment, the entire container is made of optical window material. In another embodiment, the container may be prepared (e.g., molded) from two or more separate parts, such as an optical UV-VIS-NIR transparent component for the optical window and another material (e.g., a lower-cost standard molding plastic) to make up the rest of the container. In one embodiment, the optical window is thin enough to permit spectroscopic interrogation, which will depend on the material of the window. In another embodiment, the optical window is as thin as possible to reduce interference with spectroscopic interrogation. For example, the window can have a thickness of less than about 0.20 inches, e.g., less than about 0.15, 0.10, or 0.05 inches.

Interrogation Step

Once the microorganisms have been separated, isolated and/or pelleted, the separated sample, isolated sample or pellet can undergo a second interrogation step to identify and/or characterize the microorganisms in the sample or pellet. In accordance with this invention, the interrogation takes place in a non-invasive manner, that is, the pellet is interrogated while it remains in the container. In other words the container remains sealed throughout the interrogation. The ability to identify the microorganisms in a non-invasive manner, optionally coupled with keeping the container sealed throughout the separation and identification/characterization process and automating some or all of the procedure avoids the constant handling of contaminated and/or infectious samples and greatly increases the safety of the entire process. Furthermore, the ability to characterize and/or identify microorganisms by direct interrogation without further processing of the sample or pellet (e.g., resuspension, plating, and growth of colonies), greatly increases the speed with which identification/characterization can be made.

Useful method of interrogation can include those disclosed in following co-assigned U.S. patent applications: (1) U.S. Ser. No. 12/589,929, entitled "Method for the Isolation and Identification of Microorganisms", filed Oct. 30, 2009; (2) U.S. Ser. No. 12/589,952, entitled "Method for Separation, Characterization and/or Identification of Microorganisms using Spectroscopy", filed Oct. 30, 2009; (3) U.S. Ser. No. 12/589,936, entitled "Method for Separation, Characterization and/or Identification of Microorganisms using Mass Spectrometry", filed Oct. 30, 2009; and (4) U.S. Ser. No. 12/589,976, entitled "Method for Separation, Characterization and/or Identification of Microorganisms using Raman Spectroscopy", filed Oct. 30, 2009. These applications are incorporated herein by reference.

In some embodiments, the isolated sample or pellet can be interrogated spectroscopically. In one embodiment, optical spectroscopic methods can be used to analyze one or more intrinsic properties of the microorganisms, e.g., a property present within the microorganism in the absence of additional agents, such as stains, dyes, binding agents, etc. In other embodiments, optical spectroscopic methods can be used to analyze one or more extrinsic properties of the microorganisms, e.g., a property that can only be detected with the aid of additional agents. The interrogation can be carried out using, for example, fluorescence spectroscopy, diffuse reflectance spectroscopy, infrared spectroscopy, terahertz spectroscopy, transmission and absorbance spectroscopy, Raman spectroscopy, including Surface Enhanced Raman Spectroscopy (SERS), Spatially Offset Raman spectroscopy (SORS), transmission Raman spectroscopy, and/or resonance Raman spectroscopy. To enhance Raman (SERS) and fluorescence signals, microorganisms could either be coated with gold and/or silver nanoparticles prior to centrifugation, and/or the inner optical surface could be pre-coated with metal colloids of particular size and shape (refs: Lakowicz, *Anal. Biochem.* 337:171 (2005) for fluorescence; Efrima et al., *J. Phys. Chem. B.* (*Letter*) 102:5947 (1998) for SERS). In another embodiment, the nanoparticles are present in the density cushion prior to centrifugation and associate with microorganisms as the microorganisms pass through the density cushion. In still further embodiments, the isolated sample or pellet can be interrogated using more than one means. For example, the isolated sample or pellet can be interrogated using fluorescence spectroscopy and Raman spectroscopy. In accordance with this embodiment, these interrogation steps may be carried out sequentially or simultaneously.

In accordance with this invention, the isolated sample or pellet is interrogated while it remains in the container. The container can be interrogated through an optical window in the container. The optical window may be on the bottom and/or any side or sides and/or on the top of the container. In one embodiment, the container fits into or can be fitted into a holder in a spectrometer in a suitable position for interrogation. The spectroscopic interrogation can be carried out by any technique known to those of skill in the art to be effective for detecting and/or identifying one or more intrinsic or extrinsic properties of microorganisms. For example, front face fluorescence (where the exciting and emitted light enters and leaves the same optical surface, and if the sample is generally optically thick, the excitation light penetrates a very short distance into the sample (see, e.g., Eisinger, J., and J. Flores, "Front-face fluorometry of liquid samples," *Anal. Biochem.* 94:15 (1983))) can be used for identification of microorganisms in pellets. Other forms of measurement, such as epifluorescence, reflectance, absorbance, and/or scatter measurements, can also be employed in the present invention.

Useful illumination or excitation sources, discrimination means, and detectors useful in the first interrogation step, described above as well as in the co-assigned U.S. patent applications mentioned above, are also useful for the second interrogation step.

Like the first illumination step, discussed above, the second spectroscopic technique can also be used to obtain measurements that are preferably provided as Excitation-Emission Matrix (EEM) measurements.

Furthermore, in accordance with one embodiment of the invention, it has been found that a front-face fluorescence spectroscopy provides an advantage in measuring the fluorescence and/or reflectance properties of highly scattering and highly quenching samples in the second interrogation step.

Again, like the first interrogation step described above, control measurements can be taken for known microorganisms, thus allowing for correlation of measured test data with characterization of the microorganisms of interest using various mathematical methods known to those skilled in the art. For example, the data from samples may be compared with the baseline or control measurements utilizing software systems known to one skilled in the art. More particularly, the data may be analyzed by a number of multivariate analysis methods, such as, for example, General Discriminant Analysis (GDA), Partial Least Squares Discriminant Analysis (PLSDA), Partial Least Squares regression, Principal Component Analysis (PCA), Parallel Factor Analysis (PARAFAC), Neural Network Analysis (NNA) and/or Support Vector Machine (SVM). These methods may be used to classify unknown microorganisms of interest into relevant groups based on existing nomenclature, and/or into naturally occurring groups based on the organism's metabolism, pathogenicity and/or virulence in designing the system for monitoring, detecting and/or characterizing the organism as described previously.

In yet another embodiment, non-spectroscopic measurements from the detection system, such as detection times and growth rates can be used to assist in the characterization and/or identification of microorganisms from the isolated sample or pellet. Additionally, measurements taken from a photographic image of the lower region of the separation device can provide valuable information on the identity of the isolate, such as pellet size, shape, color and density.

In some embodiments of the invention, characterization and/or identification of the microorganisms in the isolated sample or pellet need not involve identification of an exact species. Characterization encompasses the broad categorization or classification of microorganisms as well as the actual identification of a single species. Classification of microorganism from an isolated sample or pellet may comprise determination of phenotypic and/or morphologic characteristics for the microorganism. For example, characterization of the microorganisms may be accomplished based on observable differences, such as, composition, shape, size, clustering and/or metabolism. In some embodiments, classification of the microorganisms of interest may require no prior knowledge of the characteristics of a given microorganism but only requires consistent correlations with empiric measurements thus making this method more general and readily adaptable than methods based on specific binding events or metabolic reactions. As used herein "identification" means determining to which family, genus, species, and/or strain a previously unknown microorganism belongs to. For example, identifying a previously unknown microorganism to the family, genus, species, and/or strain level.

In some instances, characterization encompasses classification models which provide sufficient useful information for action to be taken. As used herein, the preferred classification models comprise grouping into one or more of the following: (1) Gram Groups; (2) Clinical Gram Groups; (3) Therapeutic Groups; (4) Functional Groups; and (5) Natural Intrinsic Fluorescence Groups.

(1) Gram Groups: Within the Gram Groups classification, microorganisms may be placed into one of three broad classification categories based on their Gram staining reaction and overall size, said groups selected from one or more of the following: (a) Gram positive microorganisms that stain dark blue with Gram staining; (b) Gram negative microorganisms that stain red with Gram staining; and (c) yeast cells that stain dark blue with Gram staining, but are very large rounded cells that are distinguished from bacteria by their morphological characteristics and size.

(2) Clinical Gram Groups: The Gram Groups may be further divided into several sub-categories representing distinguishing morphological features. These sub-categories comprise all the relevant clinical information reported by an experienced laboratory technologist, and thus provide a higher level of identification than a positive or negative Gram reaction. This particular classification is very helpful because it eliminates concerns about relying on the quality of a Gram stain and/or the skill level of the technician reading the smear by providing the equivalent clinically relevant information with an automated system. More specifically, subcategories of microorganisms based on this classification model may be selected from one or more of the following: (a) cocci, which are small rounded cells; (b) diplococci, which are two small rounded cells joined together; (c) rods, which are rectangular shape; and (d) bacilli, which are rod shaped. Examples of these sub-categories that can be ascertained by additional morphological information include: (i) Gram positive cocci; (ii) Gram positive cocci in chains; (iii) Gram positive cocci in clusters (i.e., "grape-like" clusters); (iv) Gram positive diplococci; (v) Gram positive rods; (vi) Gram positive rods with endospores; (vii) Gram negative rods; (viii) Gram negative coccobacilli; (ix) Gram negative diplococci; (x) yeast; and (xi) filamentous fungi.

(3) Therapeutic Groups: The therapeutic groups comprise multiple microbial species that, when isolated from particular specimen types, are treated with the same class of antibiotics or mixture of antibiotics (e.g., as described in "*Sanford Guide to Antimicrobial Therapy* 2008"). In many cases, identity to the species level is not required by the clinician to enable a change from initial empiric therapy to a more targeted therapy because more than one species can be treated with the same choice of antibiotic(s). This classification level correctly places these "same-treatment" microorganisms into single therapeutic categories. Examples of this characterization level include the ability to distinguish highly resistant Enterobacteriacae (EB) species from sensitive EB species (*Enterobacter* spp. from *E. coli*), or fluconazole-resistant *Candida* species (*C. glabrata* and *C. kruzei*) from sensitive *Candida* species (*C. albicans* and *C. parapsilosis*), and so on.

(4) Functional Groups: According to the invention, microorganisms may also be placed into several groups based upon a mixture of metabolic, virulence and/or phenotypic characteristics. Non-fermentative organisms may be clearly distinguished from fermentative ones. Furthermore, microorganism species that produce hemolysins may be grouped separately from non-hemolytic species. In some cases, these groups represent broader categories than genus level (e.g., coliforms, Gram negative non-fermentative rods), some at the genus level (e.g., *Enterococcus, Candida*), and some with closer to species-level discrimination (e.g., coagulase-negative staphylococci, alpha-hemolytic streptococci, beta-hemolytic streptococci, coagulase-positive staphylococci, i.e., *S. aureus*).

(5) Natural Intrinsic Fluorescence ("IF") Groups: Microorganisms may also be placed into categories based on their natural tendency to group together by their innate and/or intrinsic fluorescence characteristics. Some of these groups may be common to Therapeutic and Functional Group categories. These groupings may comprise individual species, such as *E. faecalis, S. pyogenes,* or *P. aeruginosa* that have characteristic IF signatures and/or may contain small groups of organisms with relatively conserved IF signatures such as the *K. pneumoniae-K. oxytoca* or *E. aerogenes-E. cloacae* groups.

In addition to measuring intrinsic properties of microorganisms (such as intrinsic fluorescence) for identification purposes, the methods of the present invention can further comprise the use of additional identifier agents to aid in the separation and/or identification process. Agents that bind to specific microorganisms, such as affinity ligands, can be used to separate microorganisms, to identify a class or species of microorganism (e.g., through binding to a unique surface protein or receptor) and/or to identify a characteristic of the microorganism (e.g., antibiotic resistance). Useful identifier agents include, without limitation, monoclonal and polyclonal antibodies and fragments thereof (e.g., anti-Eap for *S. aureus* identification), nucleic acid probes, antibiotics (e.g., penicillin, vancomycin, polymyxin B), aptamers, peptide mimetics, phage-derived binding proteins, lectins, host innate immunity biomarkers (acute phase proteins, LPS-binding protein, CD14, mannose binding lectin, Toll-like receptors), host defense peptides (e.g., defensins, cathelicidins, proteogrins, magainins), bacterocins (e.g., lantibiotics, such as nisin, mersacidin, epidermin, gallidermin, and plantaricin C, and class II peptides), bacteriophages, and fluorescent dyes selective for nucleic acids, lipids, carbohydrates, polysaccharides, capsules/slime or proteins, or any combination thereof. If the agent does not itself give out a detectable signal, the agent can be labeled to provide a detectable signal, such as by conjugating the agent to a marker (e.g., visible or fluorescent). Markers include, without limitation, fluorescent, luminescent, phosphorescent, radioactive, and/or colorimetric compounds. The agent can be added to the microorganisms at any step in the methods of the invention, e.g., when the sample is obtained, during lysis, and/or during separation. In some embodiments, the presence of the agent in the pellet can be determined during interrogation of the pellet. Other useful identifier agents include substrates for microbial enzymes, chelating agents, photosensitizing agent, quenching agent, reducing agent, oxidizing agent, buffer, acid, base, solvent, fixative, detergents, surfactants, disinfectants (eg. alcohols, bleach, hydrogen peroxide) and toxic compounds (eg. sodium azide, potassium cyanide) and metabolic inhibitors such as cyclohexamide, etc. Similarly, many fluorescent compounds for measuring microbial cell viability, metabolism and/or membrane potential may be used as an identifier agent in the present invention.

In one aspect of the second step of the multi-step process of the present invention, the method can further comprise a step of recovering the pellet of microorganisms and performing additional tests. In one embodiment, the pellet can be recovered by aspirating off the sample medium and density cushion. In another embodiment, the pellet can be recovered by inserting a syringe into the container and aspirating out the pellet while the sample medium and density cushion remain intact. The recovered pellet can then be resuspended in a suitable medium, e.g., saline. Once resuspended, the microorganisms can be subject to any further tests that are desired, as would be known to those of skill in the art and as described above. In particular, any test requiring clean samples of microorganisms can be carried out with the resuspended microorganisms. In some embodiments, additional identification tests can be performed. Examples of identification tests include Vitek® 2, amplified and non-amplified nucleic acid tests (NAT), chromogenic and latex agglutination assays, immunoassays, (e.g., employing labeled antibodies and/or other ligands), mass spectrometry (e.g., MALDI-TOF mass spectrometry) and/or other optical spectroscopy techniques such as infrared spectroscopy (FTIR) or Raman spectroscopy. Additional characterization tests can also be performed, such as resistance to antibiotics and/or other drugs. The additional characterization may be part of a test that was started during the initial separation and identification steps of the method. For example, the detection of methicillin resistant S. aureus can begin by adding labeled penicillin to the sample prior to separation of the microorganisms. Once the pellet has been recovered and resuspended, the level of bound penicillin can be determined.

In one aspect of the invention, some or all of the method steps can be automated. Automating the steps of the methods allows a greater number of samples to be tested more efficiently and reduces the risks of human errors in handling samples that may contain harmful and/or infectious microorganisms. Of greater importance, however, automation can deliver critical results at any time of the day or night without delay. Several studies have shown that faster identification of the organisms causing sepsis correlates with improved patient care, shorter hospital stays and lower overall costs.

The present invention is further detailed in the following examples, which are offered by way of illustration and is not intended to limit the invention in any manner. Standard techniques well known in the art or the techniques specifically described below are utilized.

EXAMPLES

Example 1

Blood Culture (Culture Medium and Blood Sample) in Quartz Cuvette in Waterbath Adapter A Fluorolog® 3 fluorescence spectrophotometer system (Horiba Jobin-Yvon Inc., New Jersey) was modified with a temperature-controlled front-face cuvette holder to enable the incubation and continuous monitoring of seeded blood cultures contained in sterile cuvettes. The fluorescence was recorded using a photomultiplier tube. Fluorescence signal strength was taken at several different wavelengths and saved. The readings were compared to experimentally determined strengths for different types of microorganism. In addition, further analysis of the spectra was conducted so that microbial identification to a given level of confidence was achieved.

Seeded blood cultures were set up in autoclaved 1.0 cm screw-capped quartz cuvettes (Starna, Inc.) containing a stir bar for agitation. To the cuvette was added 2.4 mL of standard blood culture medium, 0.6 mL of fresh normal human blood and 0.05 mL of a $10^3$/mL suspension of test microorganism (approx. 10 CFU/cuvette). A sterile, septum screw cap was placed on the cuvette, and it was inserted into the front-face adapter previously described. The culture was maintained at approximately 36° C. by connecting the adapter to a recirculating water bath heated to 36° C. The cuvette was read every 45 minutes by the Fluorlog® 3 fluorescence spectrophotometer that was software controlled. A full EEM spectra was collected at each time point with an Excitation wavelength range of 260-580 nm (every 5 nm) and an Emission wavelength range of 260-680 nm (every 5 nm) for a total of 3,139 data-points per scan. Each scan took approximately 23 minutes to complete. The cultures were maintained, and measurements taken continuously, for up to 24 hours.

Examples of the changes in fluorescence signal of several Excitation-Emission wavelength pairs for E. coli and S. aureus cultures are shown in FIGS. 1A and 1B. It is clear that following the initial point of detection, the temporal changes occurring at these wavelengths are significantly different between the two organisms. Examples of the changes in diffuse reflectance signal at 465-465 nm for E. coli and S. aureus cultures are shown in FIGS. 2A and 2B. A clear difference in the shape of the curves over time was observed.

Further detailed examination of the changes in fluorescence from all 3,139 data-points of an E. coli culture revealed the presence of at least two visually-identifiable phases; change from 7-10 hrs (approximately 0-2 hours after initial detection) of culture primarily comprising the rapid initial change in the fluorescence of the culture medium, and a change from 10-15 hr (approximately 2-7 hours after initial detection) that reflects an increase of microbial intrinsic fluorophores. This phenomenon is shown in FIG. 3 as a line plot of Excitation wavelengths from about 310-320 nm and Emission wavelengths from about 345-530 nm, and in FIGS. 4A and 4B as contour plots of time-dependent changes over the entire EEM spectra. FIGS. 3, 4A and 4B demonstrate "early" and "late" phase changes that can be used for the detection and/or characterization of a biological particle. This data exemplifies the power of temporal fluorescence and scattering measurements of a growing microbial culture.

Example 2

Identification of Microorganisms Using Measurements of Microbial Pellets and Comparison to Microbial Suspensions Several investigators have previously described using right-angle fluorescence measurements of dilute suspensions of pure microorganisms in order to identify them. We compared the effectiveness of this traditional method with our novel approach of front face measurement of a sedimented microbial pellet within the base of a proprietary UV-transparent container. Further, we compared the effectiveness of two detectors for the front face measurements; a PMT detector connected to a double grating spectrometer, and a CCD detector connected to a single grating spectrometer. These experiments were conducted using microbial colonies grown on agar plates. A panel of 42 strains representing 7 species (S. aureus, S. epidermidis, E. coli, K. oxytoca, C. albicans, C. tropicalis and E. faecalis) were tested in each of the following three optical configurations:

1. A 0.40 OD at 660 nm suspension of each microorganism was prepared in 0.45% NaCl, added to a UV-transparent cuvette and full EEM's were collected at right angle using a PMT detector (traditional method)
2. A 2-3 mm thick microbial pellet was prepared in the custom-built container by centrifuging a suspension. A full EEM of the resultant pellet was collected in front face mode using the PMT detector.
3. A 2-3 mm thick microbial pellet was prepared in the custom-built container by centrifuging a suspension. A full EEM of the resultant pellet was collected in front face mode using the CCD detector.

The intrinsic fluorescence data in the EEM's were analyzed using commercially available multivariate analysis software (General Discriminant Analysis; Statistica). The results of the analyses are depicted in Table 1.

TABLE 1

| Optical Configuration | Detector Type | % Correct to Species Level |
|---|---|---|
| 1. Suspension in cuvette | PMT | 83.3 (35/42 strains correct) |
| 2. Pellet in custom optical tube | PMT | 97.6 (41/42 strains correct) |
| 3. Pellet in custom optical tube | CCD | 97.6 (41/42 strains correct) |

Surprisingly, scanning microbial pellets in front face mode significantly improved the ability to identify them using known multivariate analysis methods. Further analysis of the fluorescence EEM data revealed that the main discriminatory region for the traditional suspension-in-cuvette configuration was within the tryptophan region of the spectrum. In contrast, front face measurements of the microbial pellets resulted in several additional regions of the EEM spectrum that provided strong discriminatory power, particularly within the 360-440 nm Excitation wavelengths. This experiment also demonstrated the functional equivalency of the PMT and CCD detectors.

The additional intrinsic fluorescence spectral information provided by front face interrogation of a microbial pellet is both an unexpected and advantageous result.

Example 3

Figure 5:
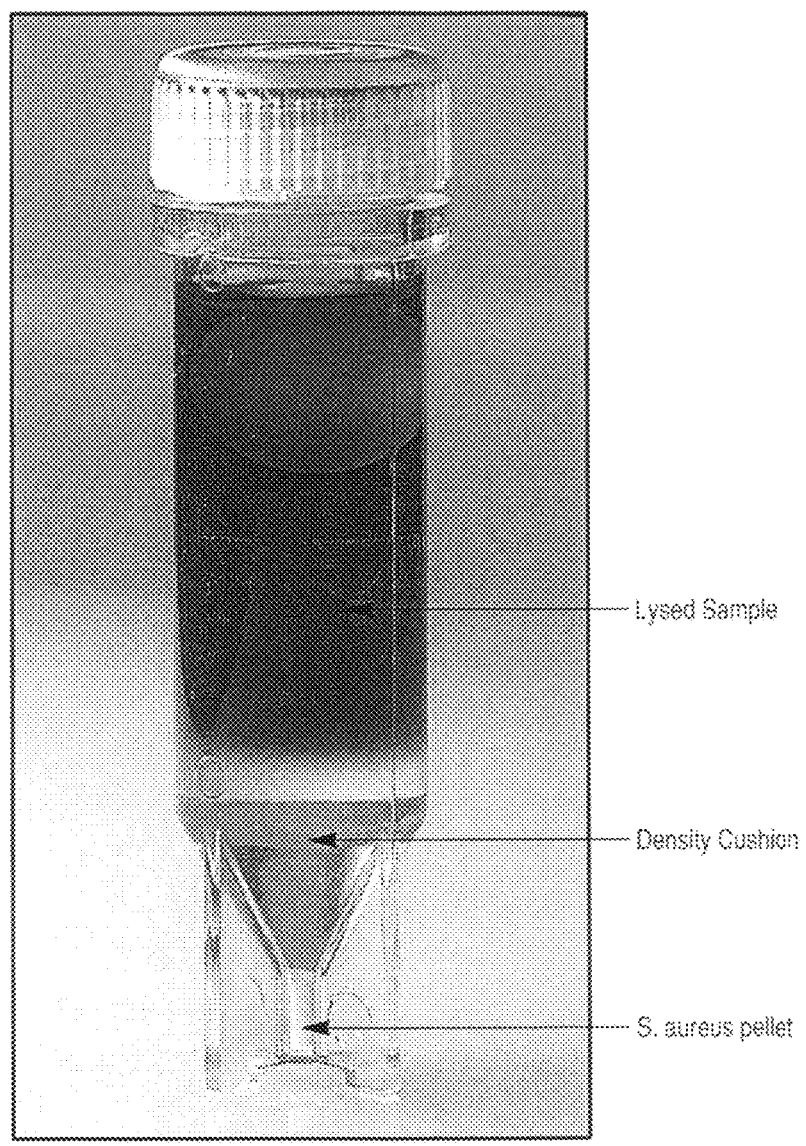
FIG. 5 is a photograph of a container showing a post-centrifugation of lysed $S.$ $aureus$-containing blood culture broth. Clearly visible in the photograph are the lysed blood culture medium, density cushion and $S.$ $aureus$ pellet.
Figure 6:
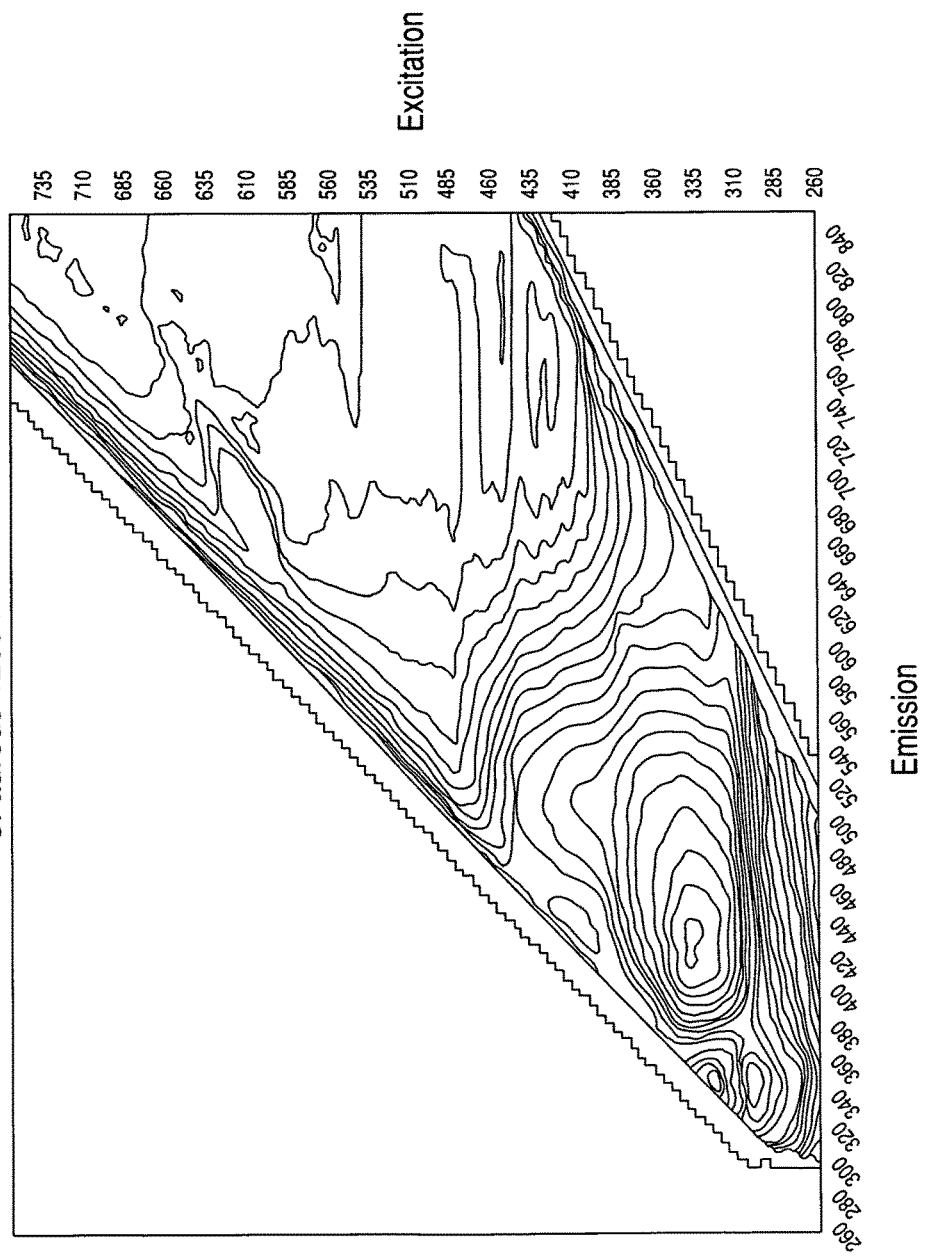
FIGS. 6-9 show examples of excitation/emission spectra for various microorganisms read in a sealed container.
Figure 7:
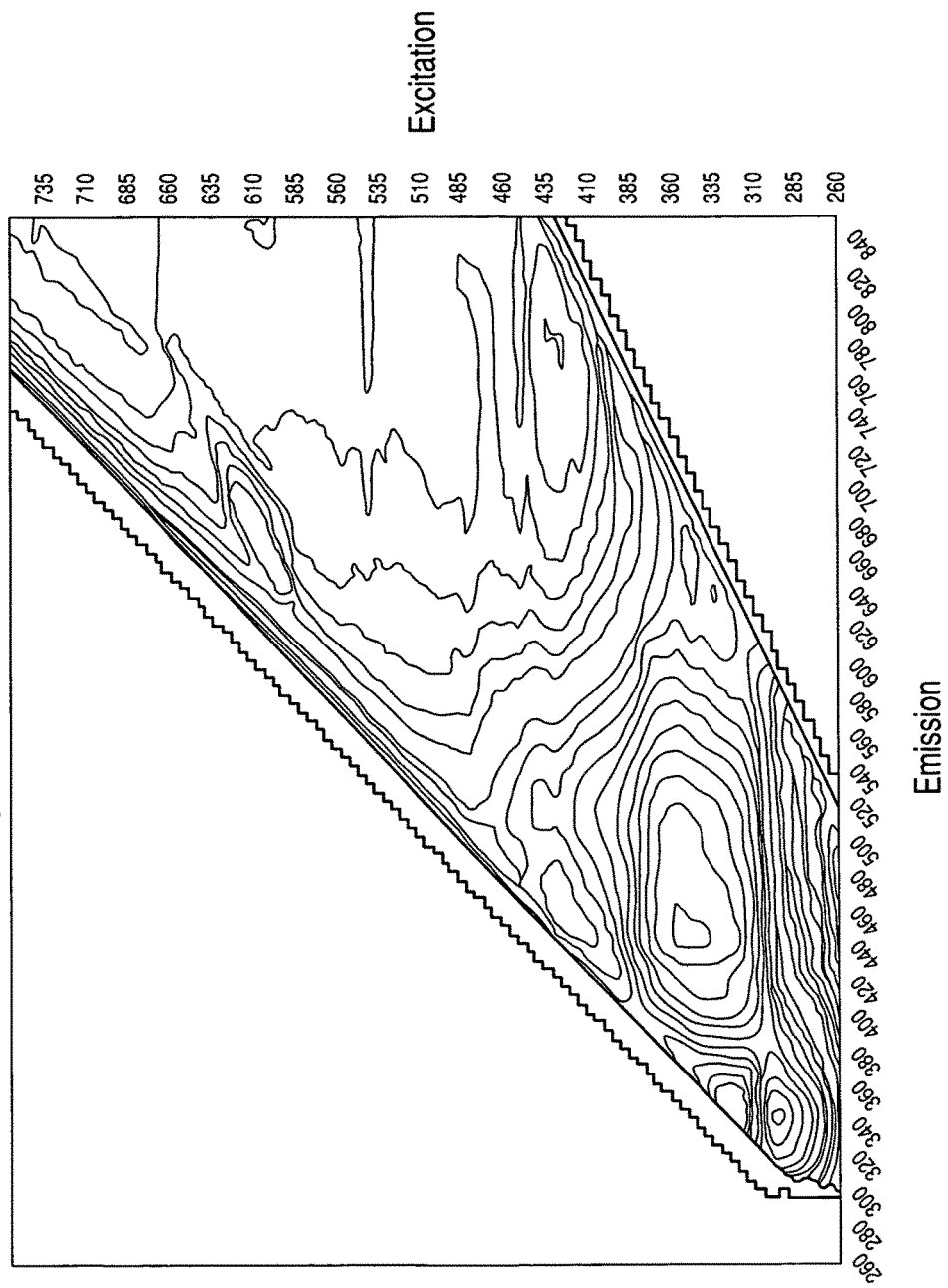
Figure 8:
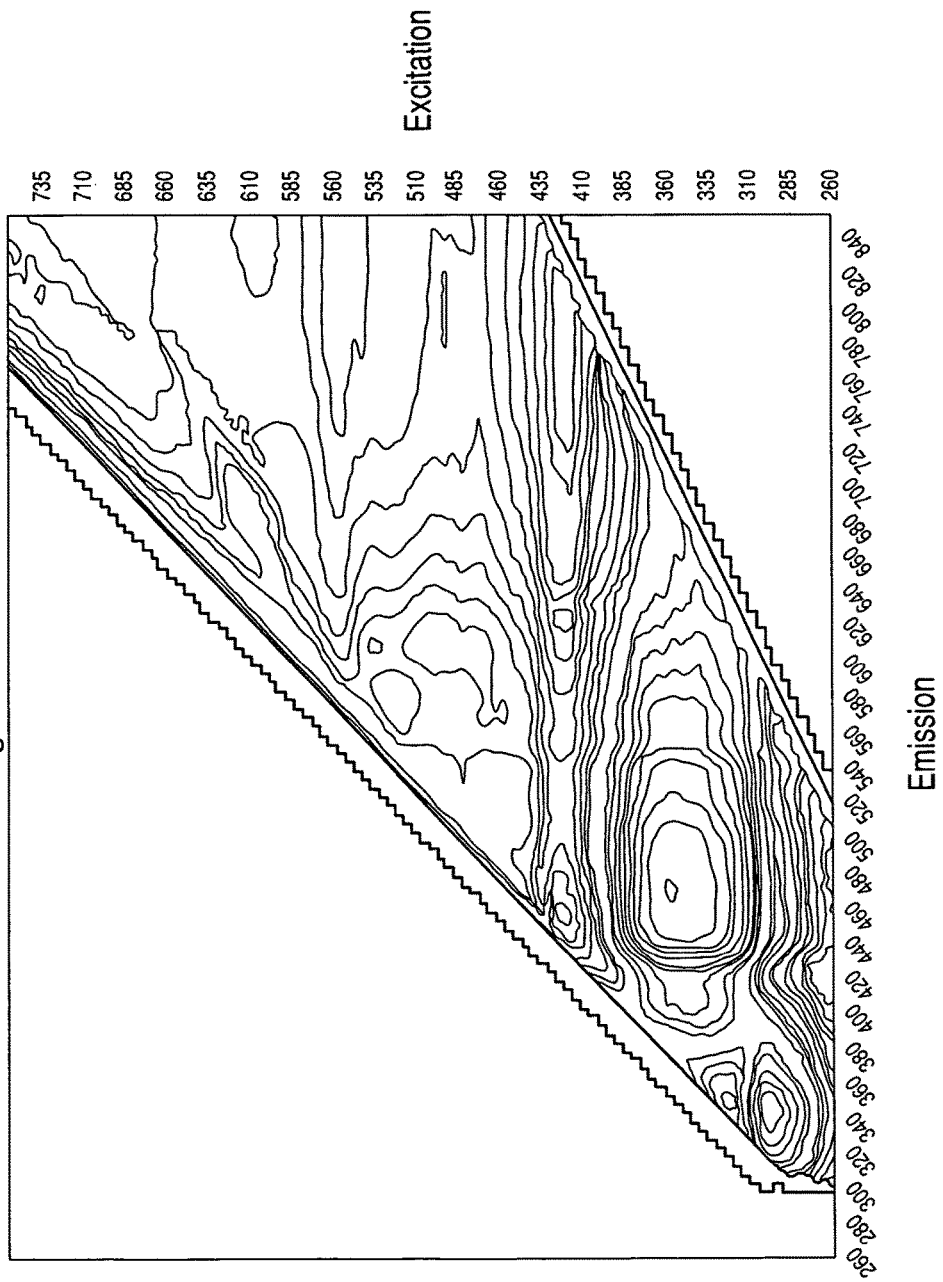
Figure 9:
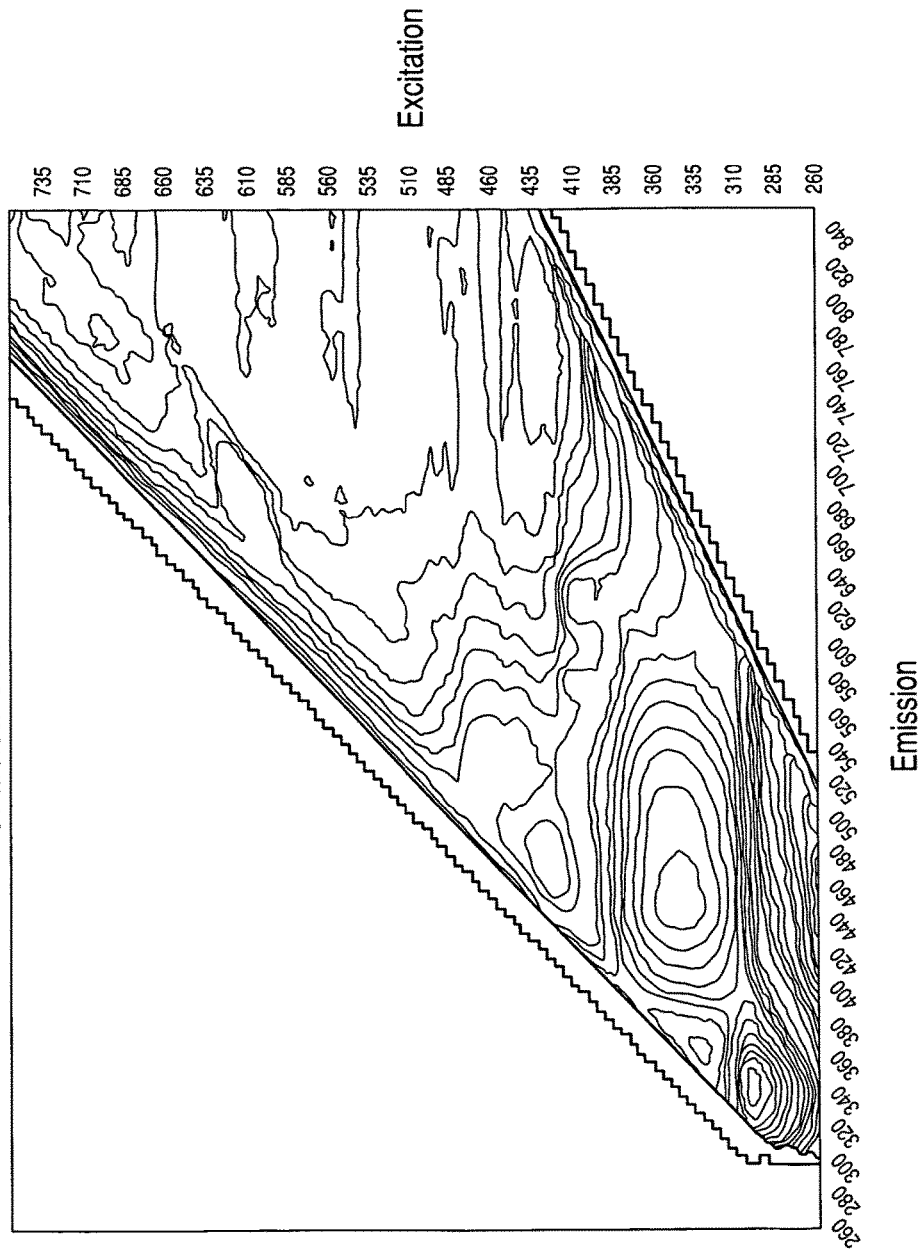

Method for the Rapid Identification of Blood Culture Isolates By Intrinsic Fluorescence To establish the utility of this method, we built a database of 373 strains of microorganisms representing the most prevalent 29 species known to cause sepsis. These organisms were "seeded" at a low inoculum into BacT/ALERT® SA bottles containing 10 mLs of human blood. Positive blood culture broth was treated as follows:
 1. A 2.0 mL sample of positive broth was mixed with 1.0 mL of selective lysis buffer (0.45% w/v Brij® 97+0.3M CAPS, pH 11.7), then placed in a 37° C. water bath 1 minute.
 2. A 1.0 mL sample of lysate was overlayed onto 0.5 mL of density cushion (24% w/v cesium chloride in 10 mM Hepes ph 7.4+0.005% Pluronic F-108) contained in a custom-built optical separation tube. A polypropylene ball was present on the surface of the density cushion to facilitate loading without disturbing the two aqueous phases.
 3. The optical separation tube was sealed with a screw-cap and centrifuged for 2 minutes at 10,000 rpm (Eppendorf® 5417R micrcentrifuge fitted with a A-8-11 swing out rotor; FIG. 5).
 4. The sealed tube was then transferred to a custom-built adapter which coupled the base of the tube directly to a 300 micron fiber optic probe connected to a spectrofluorimeter (Fluorolog® 3 from Horiba Jobin-Yvon)
 5. A full EEM scan of the purified microbial pellet was taken using the CCD detector configuration (Ex 260-850 nm, every 5 nm; Em 260-1100 nm)
 6. The EEM data was exported to Excel.

Some representative examples of the EEM spectra of microbial pellets separated from positive blood culture broth are given in FIGS. 6-9. Differences are visually evident between the species depicted, in both the magnitude and shapes of the various cellular fluorophores present.

The data was analyzed by a variety of multivariate analysis methods with the purpose of building a microbial classification database. Each scan file contained over 9,000 individual fluorescence readings, so a variety of approaches were used to minimize and normalize the data prior to analysis. As an example, Table 2 shows some preliminary results using a General Discriminant Analysis tool (Statistica). Additional input variables, such as Time-to-Detection and growth rates obtained from the BacT/ALERT® Microbial Detection System, and the amount of biomass present in the cell pellet, may be used to aid in the identification and/or characterization of the sepsis-causing isolate.

While the data in Table 2 presents identification results to the species level, any grouping level which provide the attending physician with clinically-relevant actionable information can be delivered. An example of such would be "Therapeutic" groups, where microbial species are grouped according to the antibiotics used to treat them.

The method described in the present invention satisfies the urgent need to rapidly identify microorganisms from a positive blood culture bottle in a safe and reliable manner. The results exemplified in Table 2 rival those of other identification methods that rely on growth or molecular characteristics of the microorganism, but without the time delay or cost. Furthermore, the method can be fully automated so the ID result can be sent directly to the physician via an electronic device anytime of the day or night.

The method of the present invention is also compatible with multiple diagnostic techniques due to the inbuilt separation and read sections of the custom-built container, with intact microorganisms representing the "solid phase" (FIG. 5). Examples of supplemental tests that are being developed using the concept of the present invention include, but are not limited to, measurement of microbial enzymes, cell-surface markers, nucleic acid probes and inhibitors of microbial metabolism. The method is amenable to automation and miniaturization. This method is described in detail co-pending U.S. patent application, Ser. No. 12/589,985, entitled "Methods for Separation and Characterization of Microorganisms Using Identifier Agents", filed Oct. 30, 2009, which is incorporated herein by reference.

TABLE 2

Rapid Microbial ID Method
Database was built with combined Fresh and Stored sample data (746 scans; 373 strains; 29 species) Leave-one-out cross-validation results of Fresh samples only

|  | Top Choice | [a] Low Discrim. | Within Top Two | Misclassified as: |
|---|---|---|---|---|
| C. albicans | 10/10 | 10/10 | 10/10 |  |
| C. tropicalis | 11/11 | 11/11 | 11/11 |  |
| C. parapsilosis | 11/11 | 11/11 | 11/11 |  |
| C. krusei | 12/12 | 12/12 | 12/12 |  |
| C. glabrata | 10/10 | 10/10 | 10/10 |  |
| All Yeasts: | 54/54 | 54/54 | 54/54 |  |
| % correct: | 100.0 | 100.0 | 100.0 |  |
| S. aureus | *29/30 | *29/30 | 30/30 | *S. epidermidis |
| S. epidermidis | 23/23 | 23/23 |  |  |

TABLE 2-continued

Rapid Microbial ID Method
Database was built with combined Fresh and Stored sample data (746 scans; 373 strains;
29 species) Leave-one-out cross-validation results of Fresh samples only

|  | Top Choice | [a] Low Discrim. | Within Top Two | Misclassified as: |
|---|---|---|---|---|
| S. mitis | 10/10 | 10/10 | 10/10 | |
| S. pneumoniae | *9/10 | *9/10 | 10/10 | *S. mitis |
| S. pyogenes | 11/11 | 11/11 | 11/11 | |
| S. agalactiae | 10/10 | 10/10 | 10/10 | |
| E. faecalis | 14/14 | 14/14 | 14/14 | |
| E. faecium | *12/13 | *12/13 | 12/13 | *S. mitis |
| | | | | |
| All GPC: | 118/121 | 118/121 | 120/121 | |
| % correct: | 97.5 | 97.5 | 99.2 | |
| A. baumanii | 10/10 | 10/10 | 10/10 | |
| P. aeruginosa | 20/20 | 20/20 | 20/20 | |
| S. maltophilia | 9/9 | 9/9 | 9/9 | |
| | | | | |
| All GNNF: | 39/39 | 39/39 | 39/39 | |
| % correct: | 100.0 | 100.0 | 100.0 | |
| H. influenzae | 12/12 | 12/12 | 12/12 | |
| N. meningitidis | *11/12 | 11/12 | 11/12 | *P. aeruginosa |
| | | | | |
| All Fastidious: | 23/24 | 23/24 | 23/24 | |
| % correct: | 95.8 | 95.8 | 95.8 | |
| E. aerogenes | *8/10 | 10/10 | 10/10 | *E. cloacae and K. pneumoniae |
| E. cloacaeCpx | *8/10 | 9/10 | 9/10 | *E. aerogenes (2) |
| C. freundii | 10/10 | 10/10 | 10/10 | |
| E. coli | *23/24 | 23/24 | 23/24 | *K. oxytoca |
| S. enteritidis | 11/11 | 11/11 | 11/11 | |
| K. oxytoca | *11/12 | 11/12 | 11/12 | *K. pneumoniae |
| K. pneumoniae | *13/16 | 13/16 | 15/16 | *K. oxytoca and E. aerogenes (2) |
| S. marcescens | 9/9 | 9/9 | 9/9 | |
| M. morganii | 11/11 | 11/11 | 11/11 | |
| P. mirabilis | *8/11 | 8/11 | 10/11 | *P. vulgaris (3) |
| P. vulgaris | 11/11 | 11/11 | 11/11 | |
| | | | | |
| All GNR: | 123/135 | 126/135 | 130/135 | |
| % correct: | 91.1 | 93.3 | 96.3 | |
| | | | | |
| All 29 species | 357/373 | 360/373 | 366/373 | |
| n = 373 strains | 95.7 | 96.5 | 98.1 | |

[a] = within top 2 choices and a posterior probability >0.10

Example 4

Non-Invasive Analysis of Microorganisms in Positive Blood Cultures with Lysis-Centrifugation by Raman Spectroscopy Microorganisms were "seeded" at a low inoculum into BacT/ALERT® SA bottles containing 10 mL of human blood. Blood culture broth samples were removed from bottles within a few minutes of being flagged positive by the BacT/ALERT® 3D Microbial Detection System. The samples were treated as follows:

1. A 2.0 mL sample of positive broth was mixed with 1.0 mL of selective lysis buffer (0.45% w/v Brij® 97+0.3M CAPS, pH 11.7), then placed in a 37° C. water bath for 1 minute.
2. A 1.0 mL sample of lysate was overlayed onto 0.5 mL of density cushion (24% w/v cesium chloride in 10 mM Hepes ph 7.4 +0.005% Pluronic F-108) contained in a custom-built optical separation tube. A polypropylene ball was present on the surface of the density cushion to facilitate loading without disturbing the two aqueous phases.
3. The optical separation tube was sealed with a screw-cap and centrifuged for 2 minutes at 10,000 rpm (Eppendorf® 5417R micrcentrifuge fitted with a A-8-11 swing out rotor; see FIG. 4).
4. The sealed tube was transferred to a custom-built adapter which facilitated interrogation of the microbial pellet in the base of the tube by a Model RxN1 Raman microscope (Kaiser Optical Systems Inc., Michigan) at an illumination wavelength of 785 nm. Spectra were also recorded of empty separation tubes to establish baseline Raman spectra of the plastic.

FIG. 10 shows the Raman spectra taken through the plastic separation tube both with and without a microorganism pellet. In this mode, the spectra are dominated by Raman bands from the plastic itself; however, bands unique to the microorganisms are visible only in the spectrum of the microbial pellet at wavenumbers near 1227/cm, 1583/cm, and 1660/cm. Other microorganism bands are also present, but are obscured by the stronger plastic bands at this scale.

FIG. 11 shows the Raman spectra of three microorganisms after the background has been removed by subtracting the spectrum of the empty plastic separation tube. While this background subtraction is not 100% effective, the spectral bands of the microorganisms are clearly visible. Other acquisition geometries, such as spacially offset or transmission acquisition, are likely to improve the background compensation further (see, e.g., U.S. patent appl. publ. nos. 2008/0129992 and 2009/0244533).

The foregoing Examples are illustrative of the present invention, and are not to be construed as limiting thereof. The invention is defined by the following claims, with That which is claimed is:

1. A method for detecting and identifying an unknown microorganism that may be present in a test sample, said method comprising:
   (a) inoculating a specimen container comprising a culture medium with said test sample;
   (b) detecting growth of said unknown microorganism in said specimen container using a first spectroscopic technique to obtain at least two time-dependent measurements of a growth composition comprising said sample and correlating said measurements to indicate growth of said unknown microorganism in said culture medium;
   (c) subsequently separating said unknown microorganism from said culture medium by centrifugation of said test sample through a homogeneous density cushion to generate a microorganism pellet;
   (d) interrogating the microorganism pellet in situ using front face mode intrinsic fluorescence spectroscopy to produce measurements; and
   (e) identifying said unknown microorganism in the microorganism pellet to the species level based on the produced intrinsic fluorescence measurements; and
   wherein steps (b), (c), and (d) are carried out in a sealed container and wherein said interrogation step (d) is non-invasive.

2. The method of claim 1, wherein said sample is a clinical sample and said growth composition is a liquid culture media.

3. The method of claim 2, wherein said clinical sample is selected from the group consisting of blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates.

4. The method of claim 1, wherein the sample is a non-clinical sample and is selected from the group consisting of foodstuffs, beverages, pharmaceuticals, cosmetics, water, air, soil, plants, blood products, and donor organ or tissue samples.

5. The method according to claim 1 wherein said first spectroscopic technique provides measurements for characterizing said microorganism into one or more classification models selected from the group consisting of Gram Groups, Clinical Gram Groups, Therapeutic Groups, and Functional Groups.

6. The method according to claim 1 wherein said first spectroscopic technique comprises front-face fluorescence and diffuse reflectance, and said composition comprises a liquid culture media.

7. The method according to claim 6 wherein the spectroscopic technique comprises exciting the sample at a time-interval of from about every five minutes to about every hour.

8. The method according to claim 1 wherein said growth detection correlation comprises a comparison of said at least two time-dependent measurements with control measurements taken for known microorganisms.

9. The method of claim 1, wherein said fluorescence spectroscopy interrogation step (d) is used to provide excitation-emission matrix (EEM) measurements.

10. The method of claim 1, wherein said sample is a blood sample, and wherein said method further comprises a selective lysis step for selectively lysing blood cells prior to said separation step (c), and wherein said lysis step comprises adding a lysis solution to the culture medium and sample, followed by selectively lysing said non-microorganism cells by sonication and/or by osmotic shock.

11. The method of claim 10, wherein said lysis solution comprises one or more detergents and/or one or more enzymes.

12. The method of claim 11, wherein said one or more detergents is selected from the group consisting of octylphenol ethoxylate, NP-40, polyoxyethylene detergent, (Octylphenoxy)polyethoxyethanol, polyoxyethylene 10 oleoyl ether, CHAPS, octyl β-D-glucopyranoside, saponin, nonaethylene glycol monododecyl ether, sodium dodecyl sulfate, N-laurylsarcosine, sodium deoxycholate, bile salts, hexadecyltrimethylammonium bromide, SB3-10, SB3-12, amidosulfobetaine-14, C7BzO, polyoxyethylene (20) oleyl ether, polyoxyethylene 20 cetyl ether, polyoxyethylene (23) lauryl ether, polyoxyethylenesorbitan monooleate, polyoxyethylene sorbitol ester, polyoxyalkylene ether, non-detergent sulfobetaines, amphipols, and methyl-β-cyclodextrin.

13. The method of claim 10, wherein said lysis solution further comprises an enzyme composition comprising one or more proteinases.

14. The method of claim 10, wherein said lysed sample is layered on a density cushion in a container.

15. The method of claim 14, wherein said density cushion is selected from the group consisting of colloidal silica, iodinated contrast agents, sucrose, microscope immersion oil, mineral oil, silicone oil, fluorosilicone oil, silicone gel, diatrizoate-dextran, carboxymethyl cellulose, hydroxypropylmethyl cellulose, polyethylene oxide (high molecular weight), polyoxyalkylene ether, polyacrylic acid, cross-linked polyvinyl alcohol, cross-linked polyvinyl pyrrolidine, PEG methyl ether methacrylate, pectin, agarose, xanthan, gellan, Gellan Gum, sorbitol, a sucrose and epichlorohydrin copolymer, glycerol, dextran, glycogen, cesium chloride, perfluorocarbon fluids, hydrofluorocarbon fluid, and combinations thereof.

16. The method of claim 14, wherein said density cushion has a density of about 1.025 to about 1.120 g/ml.

* * * * *